(12) United States Patent
Dragsdorf

(10) Patent No.: US 12,016,778 B2
(45) Date of Patent: Jun. 25, 2024

(54) IMPLANTABLE JOINT HAVING HEATING SYSTEM

(71) Applicant: Roger D. Dragsdorf, Gig Harbor, WA (US)

(72) Inventor: Roger D. Dragsdorf, Gig Harbor, WA (US)

( * ) Notice: Subject to any disclaimer, the term of this patent is extended or adjusted under 35 U.S.C. 154(b) by 0 days.

(21) Appl. No.: 18/206,224

(22) Filed: Jun. 6, 2023

(65) Prior Publication Data
US 2023/0390069 A1 Dec. 7, 2023

Related U.S. Application Data

(60) Provisional application No. 63/349,419, filed on Jun. 6, 2022.

(51) Int. Cl.
| | |
|---|---|
| *A61F 7/00* | (2006.01) |
| *A61F 2/30* | (2006.01) |
| *A61F 2/32* | (2006.01) |
| *A61F 2/38* | (2006.01) |
| *A61F 2/40* | (2006.01) |

(52) U.S. Cl.
CPC .......... *A61F 2/30721* (2013.01); *A61F 7/007* (2013.01); *A61F 2002/30668* (2013.01); *A61F 2/32* (2013.01); *A61F 2/38* (2013.01); *A61F 2/40* (2013.01); *A61F 2007/0023* (2013.01); *A61F 2007/003* (2013.01); *A61F 2007/0042* (2013.01); *A61F 2007/0077* (2013.01); *A61F 2007/0086* (2013.01); *A61F 2007/0096* (2013.01)

(58) Field of Classification Search
CPC .... A61F 7/02; A61F 7/12; A61F 7/007; A61F 2002/465; A61F 2002/30668; A61F 2002/0077; A61F 2002/0086; A61N 1/08; A61N 1/40

See application file for complete search history.

(56) References Cited

U.S. PATENT DOCUMENTS

| | | | |
|---|---|---|---|
| 5,507,814 | A | 4/1996 | Gilbert et al. |
| 7,190,273 | B2 | 3/2007 | Liao et al. |
| 7,497,613 | B2 | 3/2009 | King et al. |
| 10,314,619 | B2 | 6/2019 | Roschak et al. |
| 10,441,171 | B2 | 10/2019 | Windolf |

(Continued)

FOREIGN PATENT DOCUMENTS

| | | |
|---|---|---|
| EP | 2 839 806 A1 | 2/2015 |
| WO | WO 2014/045312 A1 | 3/2014 |

*Primary Examiner* — Brian A Dukert
(74) *Attorney, Agent, or Firm* — Constellation Law Group, PLLC; Dale C. Barr

(57) ABSTRACT

Devices that are implantable within a patient's body, and more specifically, to implantable joints (e.g. hip joint, knee joint, shoulder joint, etc.) having a heating system. For example, a device implantable within a patient's body may include a first member configured to be coupled to a first bone and a second member configured to be coupled to a second bone, the first and second members being operatively coupled to form a moveable joint. A heating system may be configured to controllably heat at least a portion of the at least one of the first and second members. The heating system may include a controller operable to cause a heating element to apply heat based on one or more external conditions (e.g. temperature, humidity, etc.).

22 Claims, 14 Drawing Sheets

(56) References Cited

U.S. PATENT DOCUMENTS

| | | |
|---|---|---|
| 10,898,254 B2 | 1/2021 | Diederich et al. |
| 10,932,787 B2 | 3/2021 | Plaza et al. |
| 11,653,391 B2 | 5/2023 | Van der Walt et al. |
| 2008/0262580 A1* | 10/2008 | Gerber ............... A61F 7/12 607/113 |
| 2009/0130632 A1 | 5/2009 | Tsuru et al. |
| 2010/0145412 A1* | 6/2010 | Boyden ............ A61L 2/0011 607/60 |
| 2013/0090707 A1 | 4/2013 | Doerr et al. |
| 2018/0161039 A1 | 6/2018 | Harks |
| 2019/0159725 A1 | 5/2019 | Chopra et al. |
| 2020/0121495 A1 | 4/2020 | Nelson et al. |

\* cited by examiner

IMPLANTABLE JOINT HAVING HEATING SYSTEM

CROSS REFERENCE TO RELATED APPLICATIONS

This patent application claims priority benefits under 35 USC § 119(e) from the following provisional patent application: U.S. Patent Application No. 63/349,419 filed on Jun. 6, 2022, which application is incorporated herein by reference.

FIELD OF THE DISCLOSURE

The present disclosure relates generally to devices that are implantable within a patient's body, and more specifically, to implantable joints having a heating system.

BACKGROUND

Artificial joints (e.g. hip, shoulder, knee, etc.) are routinely implanted within a patient's body. Prior art devices lack desirable capabilities, however, and there is room for improvement.

SUMMARY

The present disclosure is directed to systems and methods for implantable joints having a heating system. Embodiments of implantable joints in accordance with the present disclosure may advantageously provide warming to compensate for cold, arthritis, dampness, or other conditions, thereby helping to reduce and possibly eliminate aches and pains in the person and improving the comfort of the implantable joint for the patient.

For example, in some embodiments, a device implantable within a patient's body comprises: a first member configured to be coupled to a first bone and a second member configured to be coupled to a second bone, the first and second members being operatively coupled to form a moveable joint; and a heating system operatively coupled to at least one of the first and second members and configured to controllably heat at least a portion of the first and second members. In some embodiments, the heating system includes a controller operatively coupled to a temperature sensor, the controller causing a heating element to apply heat when a lower temperature limit is sensed and to discontinue heating when an upper temperature limit is sensed. In some embodiments, the first and second members are operatively coupled to form at least one of a movable hip joint, a movable shoulder joint, or a movable knee joint. And in some embodiments, the heating system includes a power source that is wirelessly rechargeable.

It will be appreciated that in some embodiments, a heating system of an implantable joint device in accordance with the present disclosure may have an on-board power supply (e.g. battery, capacitor, etc.) that has sufficient capacity to perform all operations of the heating system, including providing power to the other electronic components of the heating system (e.g. controller, sensor, etc.), as well as providing power to one or more heating elements to perform the desired heating of one or more portions of the implantable joint device. Alternately, in some embodiments, the on-board power supply of the device may have only a limited storage capacity such that it may typically only provide power to one or more the non-heating components of the heating system, and the in vivo heating system may wirelessly receive power via a receiver (e.g. a resonant receiver) from an external power source to perform the desired heating using the one or more heating elements. In still further embodiments, the heating system may employ a hybrid approach whereby the power to the one or more heating elements may be provided partially by the on-board power supply and partially using power that is wirelessly received from an external power source as the implantable joint device is disposed within the patient's body.

There has thus been outlined, rather broadly, some of the embodiments of the present disclosure in order that the detailed description thereof may be better understood, and in order that the present contribution to the art may be better appreciated. There are additional embodiments that will be described hereinafter and that will form the subject matter of the claims appended hereto. In this respect, before explaining at least one embodiment in detail, it is to be understood that the various embodiments are not limited in its application to the details of construction or to the arrangements of the components set forth in the following description or illustrated in the drawings. Also, it is to be understood that the phraseology and terminology employed herein are for the purpose of the description and should not be regarded as limiting.

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evidence to the contrary from the description, where elements in different figures use identical reference numbers, the elements are generally either identical or at least similar in function or purpose.

BRIEF DESCRIPTION OF THE DRAWINGS

Embodiments of methods and systems in accordance with the teachings of the present disclosure are described in detail below with reference to the following drawings.

DETAILED DESCRIPTION

Systems and methods for implantable joints having a heating system are described herein. Many specific details of certain embodiments are set forth in the following description and in FIGS. 1-15 to provide a thorough understanding of such embodiments. One skilled in the art will understand, however, that the invention may have additional embodiments, or that alternate embodiments may be practiced without several of the details described in the following description.

Embodiments in accordance with the present disclosure relate to artificial joints that may be implanted within a person's body to repair or replace a defective joint of the person's musculoskeletal system, such as a hip joint, a knee joint, a shoulder joint, or any other suitable joints. More specifically, in some embodiments, the implantable joint may include a heating system that provides heat to at least a portion of the implantable joint. Embodiments of implantable joints having heating systems in accordance with the present disclosure may provide considerable advantages over prior art assemblies, such as improved comfort to the person during certain environmental conditions, leading to improved patient satisfaction, as described more fully below.

It will be appreciated that, in some embodiments, a device implantable within a person's body may include: a first member configured to be coupled to a first bone and a second member configured to be coupled to a second bone, the first and second members being operatively coupled to form a moveable joint; and a heating system operatively coupled to at least one of the first and second members and configured to controllably heat at least a portion of the first and second members. In some embodiments, the heating system includes a controller operatively coupled to a temperature sensor, the controller causing a heating element to apply heat when a lower temperature limit is sensed and to discontinue heating when an upper temperature limit is sensed. More specifically, in some embodiments, the first and second members are operatively coupled to form at least one of a movable hip joint, a movable shoulder joint, or a movable knee joint. And in some embodiments, the heating system includes a power source that is wirelessly rechargeable by a power source external to the person's body. Additional details and aspects of various embodiments in accordance with the present disclosure are described more fully below.

Figure 1:
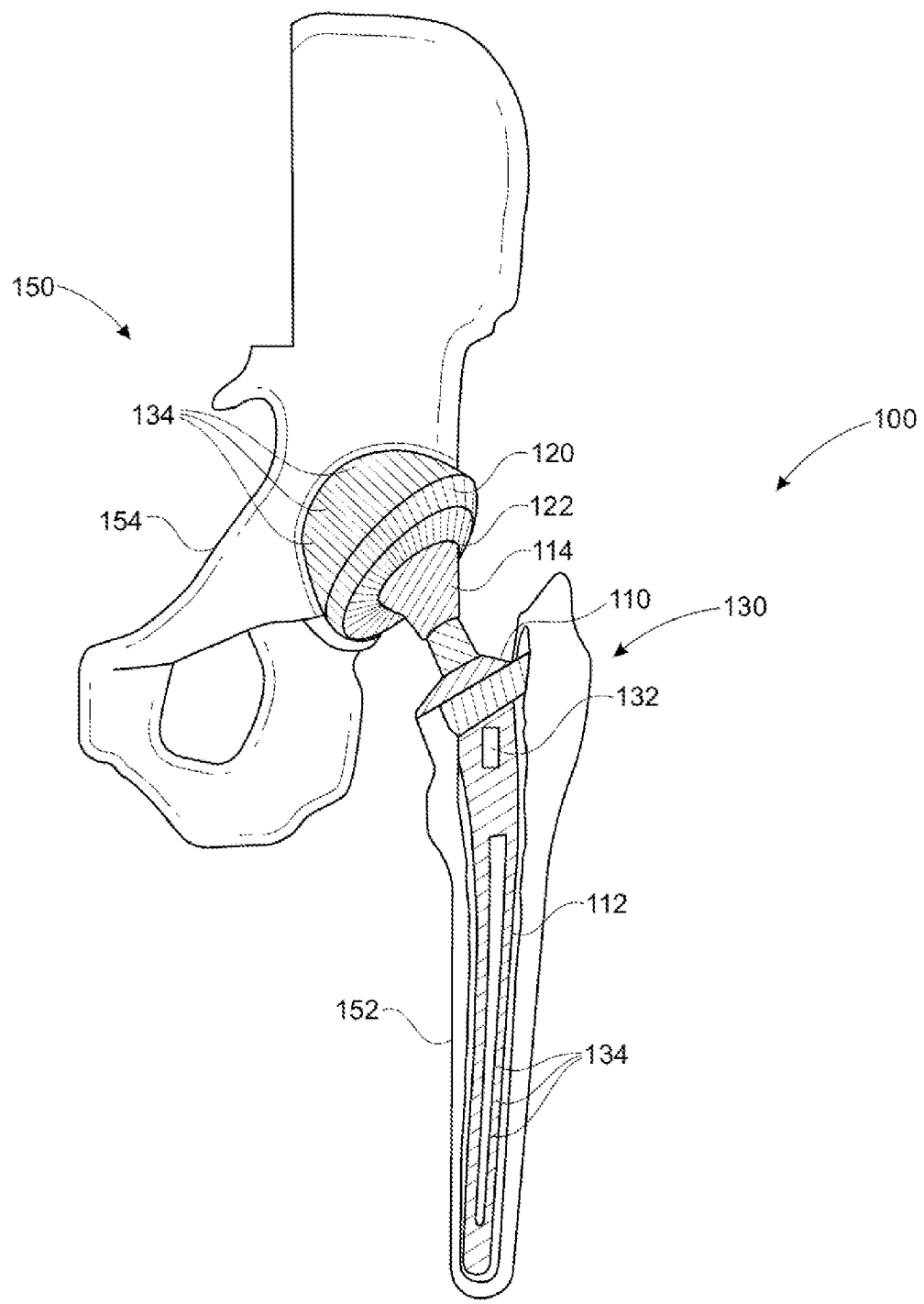
FIG. 1 is a perspective view of an implantable hip joint located in a representative environment in accordance with an example embodiment.

For example, FIG. 1 is a perspective view of an implantable hip joint 100 located in a representative environment 150 in accordance with an example embodiment. It will be appreciated that the implantable hip joint 100 may be fabricated from metal, ceramic, plastic, polymer, or any suitable combination of materials. In some embodiments, the implantable hip joint 100 includes a first member 110 configured to be coupled to a first bone 152 and a second member 120 configured to be coupled to a second bone 154. More specifically, as shown in FIG. 1, the first bone 152 may be a femur, and the second bone 154 may be a portion of a pelvis bone commonly referred to as an acetabulum. In other embodiments, the first and second members 110, 120 may be configured to be coupled to other bones or other portions of the person's skeletal system.

In some embodiments, the first member 110 includes a stem portion 112 configured to be inserted into the first bone 152 (e.g. femur), and a ball portion 114 coupled to the stem portion 112 that is configured to project outwardly from the first bone 152. The stem portion 112 may be coupled to the first bone 152 by cement, press fit, fasteners (e.g. screws, pins, etc.), or any other suitable manner. Similarly, the second member 120 may be coupled to the second bone 154 by cement, press fit, fasteners (e.g. screws, pins, etc.), or any other suitable manner. In some embodiments, the first and second members 110, 120 may be configured with porosity, apertures, surface roughness, or other similar features to enable bone growth of the first and second bones 152, 154 to engage with the first and second members 110, 120 to help secure the first and second members 110, 120 to the first and second bones 152, 154, respectively.

In some embodiments, the first and second members 110, 120 are operatively coupled to form a moveable joint. For example, in the embodiment shown in FIG. 1, the first and second members 110, 120 are operatively coupled in the manner of a hip joint of a human being. More specifically, in some embodiments, the second member 120 includes a cup portion 122 that is configured to fittingly receive the ball portion 114 of the first member 110. The ball portion 114 of the first member 110 is fittingly received into the cup portion 122 of the second member 120, enabling the first member 110 operatively move (e.g. rotate, pivot) with respect to the second member 120 to form a moveable hip joint. Of course, in other embodiments, other artificial joints may be formed.

With continued reference to FIG. 1, the implantable hip joint 100 further includes a heating system 130 operatively coupled to at least one of the first and second members 110, 120 and configured to controllably heat at least a portion of the first and second members 110, 120. In some embodiments, the heating system 130 includes a main module 132 that is operatively coupled to one or more heating elements 134. As shown in FIG. 1, in some embodiments, the heating elements 134 may be distributed over (or within) various surfaces of the first and second members 110, 120. In some embodiments, the heating elements 134 may be built into the implantable hip joint 100 and may be designed for maximum efficiency. In some embodiments, heat radiates from the heating elements 134 through some or all of the implantable hip joint 100. It will be appreciated that the heating elements 134 may include wires, resistors, coils, or any other suitable elements, and may be configured in any suitable pattern, including branches, spiderwebs, coils, straight lines, or any other suitable patterns.

In some embodiments, the main module 132 may be configured to receive one or more inputs indicative of one or more environmental conditions, and to cause the heating elements 134 to provide warmth to one or more portions of the implantable hip joint 100 and/or the surrounding bones 152, 154 and tissues of the person's body. For example, in some embodiments, the inputs to the main module 132 may be provided by one or more in vivo sensors disposed within the main module 132, or by one or more sensors disposed elsewhere on the implantable hip joint 100, or even elsewhere within the person's body. Similarly, in some embodiments, the inputs to the main module 132 may be provided by one or more external sensors disposed outside the person's body.

Figure 2:
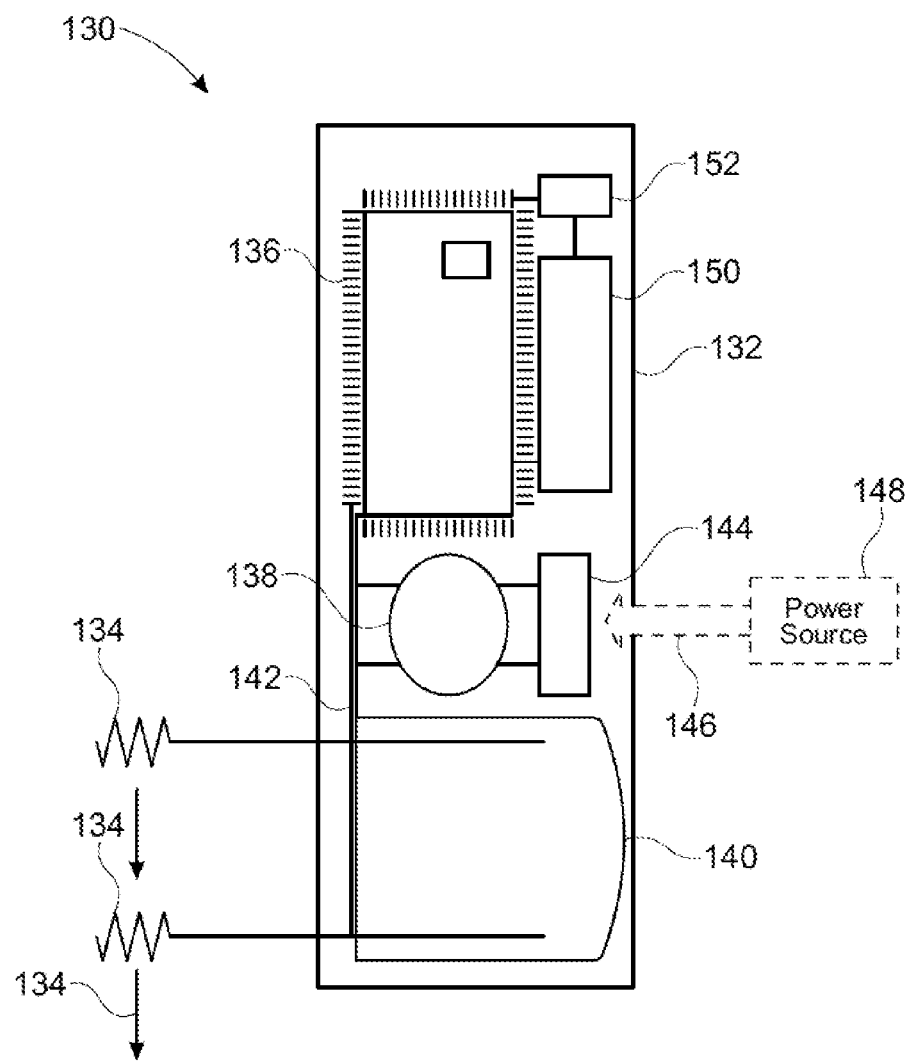
FIG. 2 is an enlarged schematic view of a main module of a heating system of the implantable hip joint of FIG. 1 in accordance with an example embodiment.

FIG. 2 is an enlarged schematic view of the main module 132 of the heating system 130 of the implantable hip joint 110 of FIG. 1 in accordance with an example embodiment. In some embodiments, the main module 132 includes a controller 136 (e.g. a microcontroller) operatively coupled to a battery 138 and to a temperature sensor 140 via a bus 142. In some embodiments, temperature sensor 140 may be a thermistor, a thermocouple, a semiconductor element, or any other suitable type of sensor. The battery 138 provides electrical power to the controller 136 and to the other components of the heating system 100, including the temperature sensor 140 and the heating elements 134. The battery 138 may, for example, be a long-life battery, such as a lithium-ion battery or the like. Accordingly, in some embodiments, the controller 136 may be configured to cause one or more of the heating elements 134 to apply heat when a lower temperature limit is sensed by the temperature sensor 140, and to discontinue heating when an upper temperature limit is sensed.

In some embodiments, the battery 138 may be a rechargeable battery. For example, in some embodiments, the battery 138 may be operatively coupled to a receiving element 144 that is configured to receive a recharging power 146 from an external power source 148 that may be positioned external to the person's body. For example, in some embodiments, the receiving element 144 may be an antenna, a transceiver, an inductive element, or any other suitable element capable of wirelessly receiving electromagnetic energy. In some embodiments, the external power source 148 may be an external battery, a wall outlet, or any other suitable power source.

As shown in FIG. 2, in some embodiments, the main module 130 may further include a thermostat 150 operatively coupled to the controller 136, and a fuse 152 operatively coupled to the controller 136. In further embodiments, one or both of the thermostat 150 and the fuse 152 may be integrated into the controller 136 rather than being separate components. In some embodiments, the thermostat 150 may be configured to monitor one or more conditions and to provide one or more signals to the controller 136 to engage or disengage power to the heating elements 134. For example, in some embodiments, the thermostat 150 may determine one or more of exterior temperature and humidity (either by measurement or by receiving signals from an external sensor), and then provide one or more signals to the controller 136 to raise (or discontinue heating) the temperature of the heating elements 134 of the implantable hip joint 100.

For example, if the thermostat 150 determines an external temperature condition that is low (i.e. cold), the thermostat 150 may provide a signal to the controller 136 that engages power from the battery 138 to at least some of the heating elements 134, providing warming energy to at least some of the implantable hip joint 100. Alternately, as one or more portions of the implantable hip joint 100 are warmed, if the thermostat 150 determines that an external temperature is at a suitable level, and the thermostat 150 may provide a signal to the controller 136 that disengages power from the battery 138 to at least some of the heating elements 134, thereby discontinuing the warming energy to at least some of the implantable hip joint 100. In some embodiments, temperature sensor 140 may monitor an internal temperature at one or more locations, and may provide feedback signals to the controller 136 to enable the controller 136 to evaluate whether the heating system 130 is operating and whether to continue, adjust, or discontinue operation of the heating system 130.

In some embodiments, the fuse 152 may open to discontinue operation of the heating system 130 in the event that an undesirable operating condition is detected (e.g. a short or other non-optimal condition). For example, in some embodiments, the fuse 152 may open to discontinue operation of the heating system 130 if the thermostat 150 fails, thereby preventing overheating of the heating elements 134 or other portions of the heating system 130. As noted above, in some embodiments, the functionalities of the thermostat 150 and the fuse 152 may be integrated into the controller 136, eliminating the need for separate thermostat 150 and fuse 152 components.

Embodiments of implantable joints (e.g. implantable hip joint 100) having heating systems (e.g. heating system 130) may provide considerable advantages over prior art assemblies. By monitoring one or more conditions, such as the external temperature and humidity, the implantable heat joint 100 may provide warming to at least partially compensate for cold, arthritis, dampness, or other conditions, thereby improving the comfort of the implantable heat joint 100 for the patient. By warming at least part of the implantable heat joint 100 during certain conditions using the heating system 130, the implantable heat joint 100 may reduce or eliminate aches and pains in the person proximate to the implantable heat joint 100 that may be caused by the body's reaction to cold, damp and implanted material not matching the body temperature. Accordingly, embodiments of implantable joints in accordance with the present disclosure (e.g. implantable hip joint 100) may advantageously provide improved comfort to the person during certain environmental conditions, leading to improved patient satisfaction.

It will be appreciated that a variety of different embodiments of implantable joints having a heating system in accordance with the present disclosure may be conceived. For example, as noted above, in some embodiments, a heating system of an implantable joint device in accordance with the present disclosure may have an on-board power supply (e.g. battery, capacitor, etc.) that has sufficient capacity to perform all operations of the heating system, including providing power to the other electronic components of the heating system (e.g. controller, sensor, etc.), as well as providing power to one or more heating elements to perform the desired heating of one or more portions of the implantable joint device. Alternately, in some embodiments, the on-board power supply of the device may have only a limited storage capacity such that it may typically only provide power to one or more the non-heating components of the heating system, and the in vivo heating system may wirelessly receive power via a receiver (e.g. a resonant receiver) from an external power source to perform the desired heating using the one or more heating elements. In still further embodiments, the heating system may employ a hybrid approach whereby the power to the one or more heating elements may be provided partially by the on-board power supply and partially using power that is wirelessly received from an external power source as the implantable joint device is disposed within the patient's body.

Figure 3:
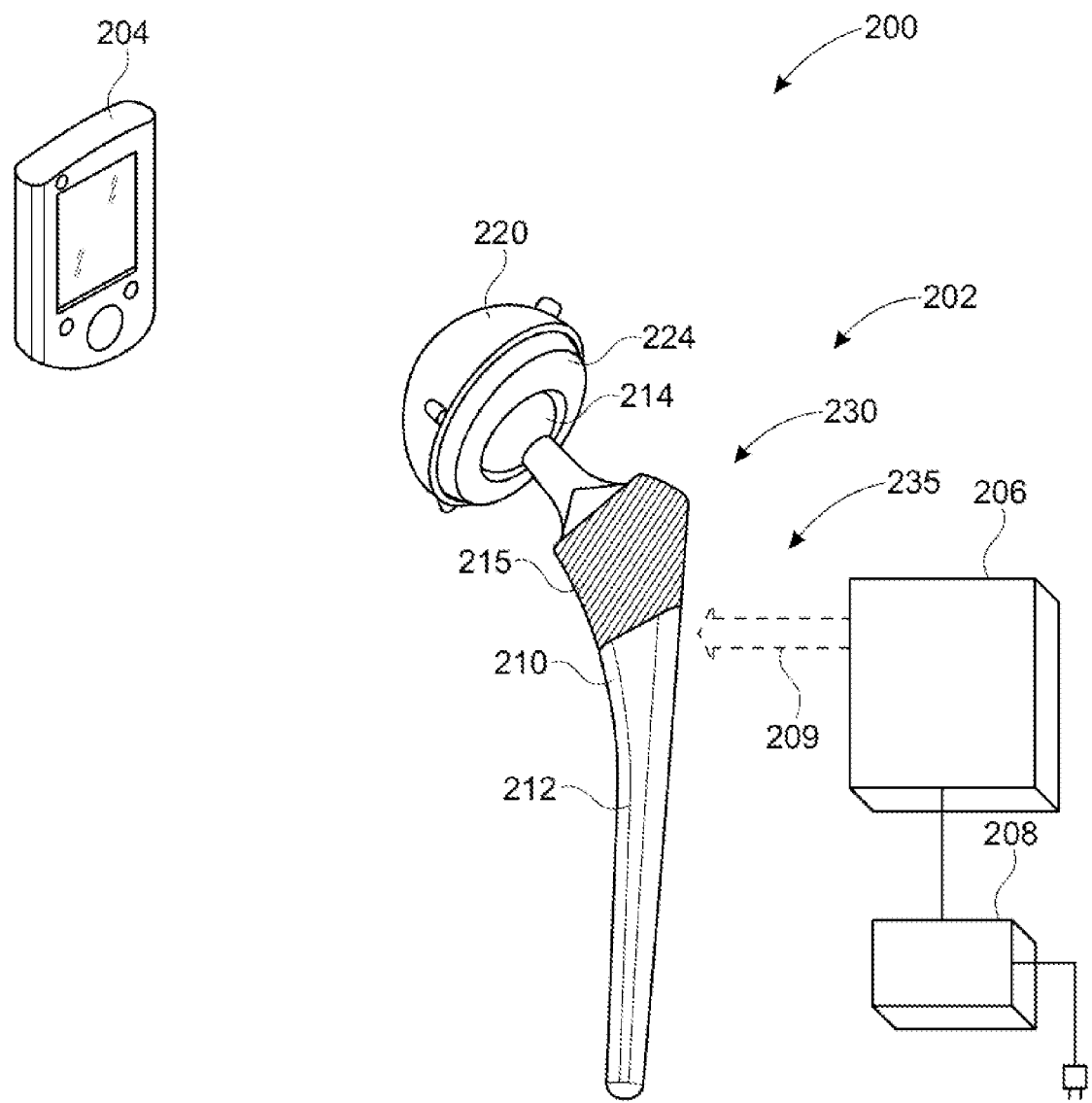
FIG. 3 is a perspective view of a system that includes an implantable hip joint in accordance with another example embodiment.

For example, FIG. 3 is a perspective view of a system 200 in accordance with another example embodiment. In the embodiment shown in FIG. 3, the system 200 includes an implantable hip joint 202, a monitoring component 204, a power pack 206, and a charging component 208. In some embodiments, the monitoring component 204 may be a handheld device, such as a cellular telephone (or smart watch, personal data assistant, tablet, laptop, etc.), having various communication and input/output functionalities that enable a user to monitor and provide inputs and commands to other components of the system 200, including the components of the implantable hip joint 202 and the power pack 206.

In some embodiments, the power pack 206 may be a device that stores power that may be provided to the implantable hip joint 202. More specifically, in some embodiments, the power pack component 206 may be a portable, rechargeable device that may be carried with the patient to provide a heating power 209 to the implantable hip joint 202 as needed during normal day-to-day activities. More specifically, in some embodiments, the heating power 209 may be provided by a wireless power link 235 between the implantable hip joint 202 and the power pack 206. In some embodiments, the charging component 208 may include a charging cable or other suitable device that may be coupled to the power pack 206 and to a power supply (e.g. a wall outlet, a generator, etc.) to recharge the power pack 206 after use. In some embodiments, the implantable hip joint 202 may include an on-board power supply that is sufficient for non-heating power requirements, such as for on-board electronics during non-heating operations, such that the on-board power supply need not be configured to provide the power for a heating system of the implantable hip joint 202. Additional aspects of the components of the system 200 are described more fully below.

Figure 4:
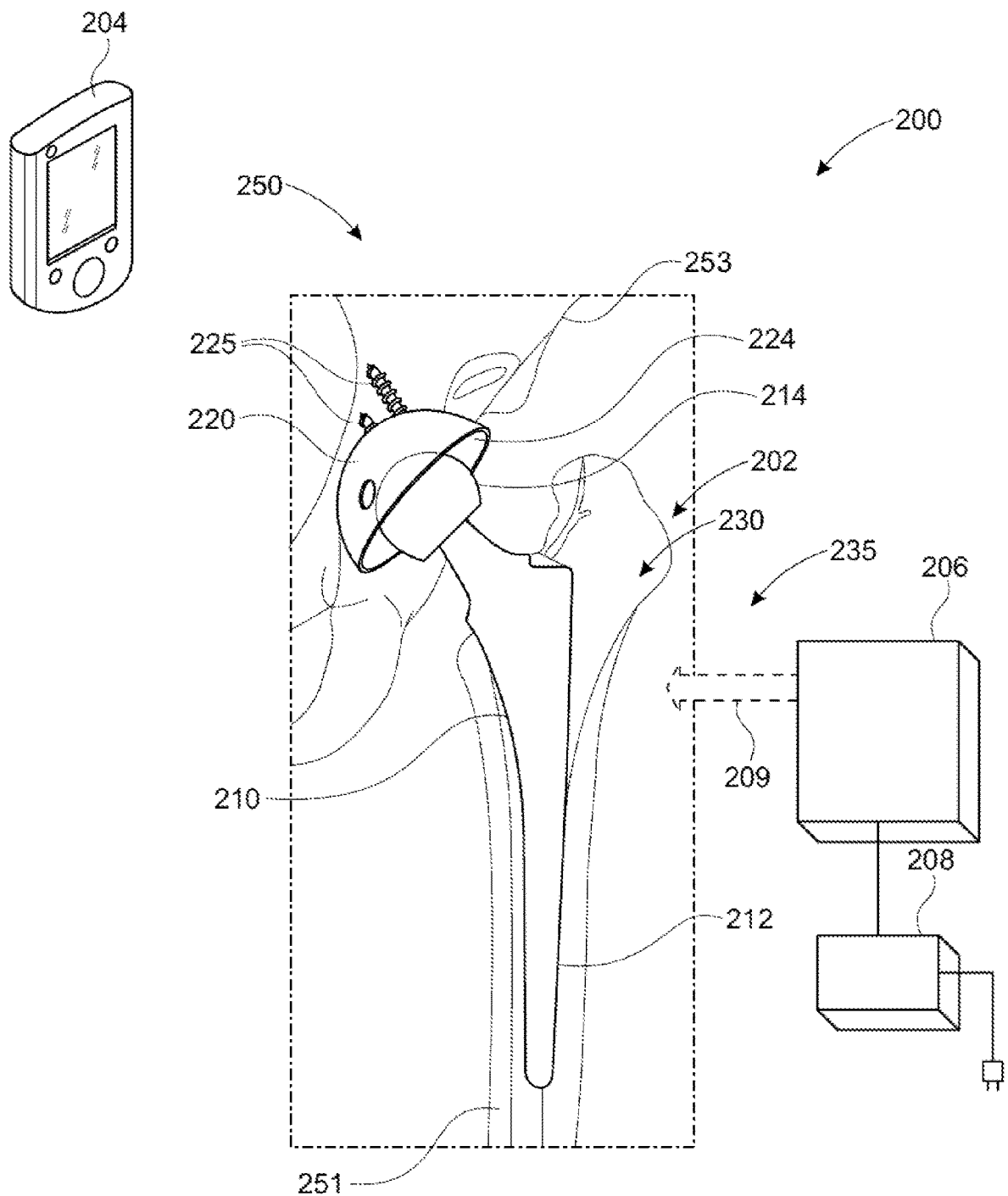
FIG. 4 is a perspective view of the system and the implantable hip joint of FIG. 3 disposed within a representative environment in accordance with another example embodiment.
Figure 5:
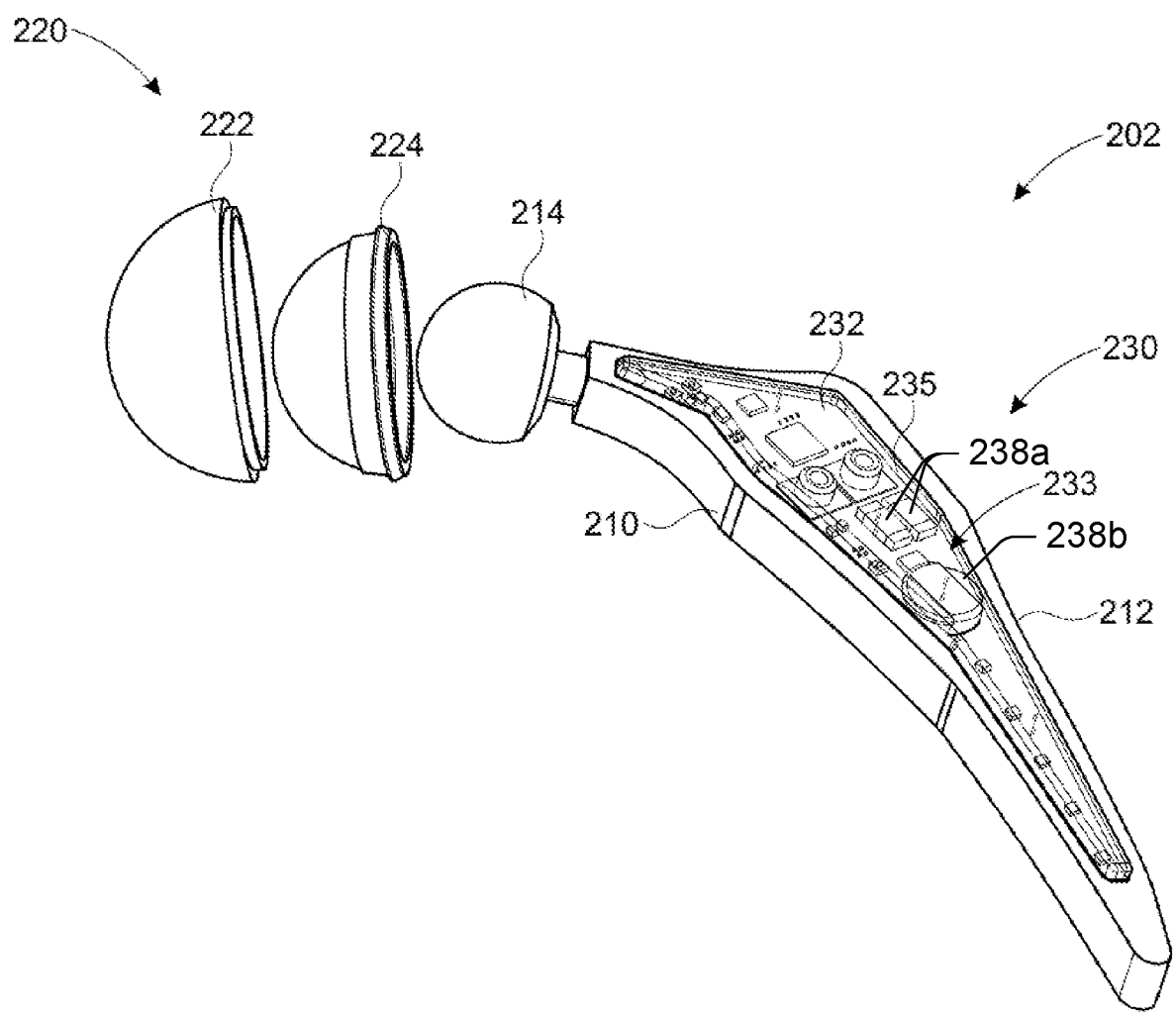
FIG. 5 is a partially-exploded view of the implantable hip joint of FIG. 3 in accordance with an example embodiment.
Figure 6:
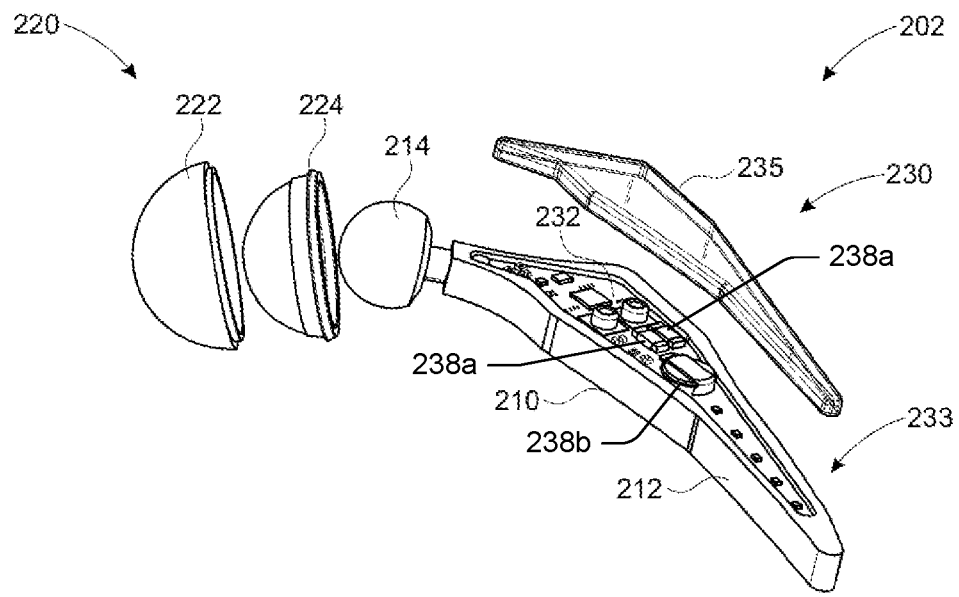
FIG. 6 is another partially-exploded view of the implantable hip joint of FIG. 3 in accordance with an example embodiment.
Figure 7:
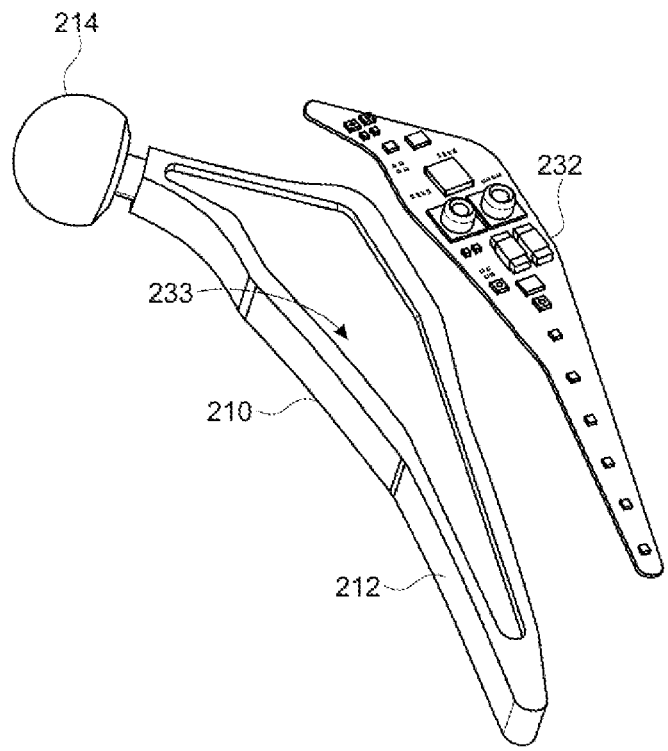
FIG. 7 is yet another partially-exploded view of the implantable hip joint of FIG. 3 in accordance with an example embodiment.

FIG. 4 is a perspective view of the system 200 of FIG. 3 with the implantable hip joint 202 disposed within a representative environment 250. FIGS. 5-7 are partially exploded views of the implantable hip joint 202 of FIG. 3. In the embodiment shown in FIGS. 3-7, the implantable hip joint 200 includes a first member 210 configured to be coupled to a first bone 251 and a second member 220 configured to be coupled to a second bone 253. As described above, the first bone 251 may be a femur and the second bone 253 may be a portion of a pelvis bone (e.g. an acetabulum). In some embodiments, the first member 210 includes a stem portion 212 configured to be inserted into the first bone 251 (e.g. femur), and a ball portion 214 coupled to the stem portion 212 that is configured to project outwardly from the first bone 251. The stem portion 212 may be press fit into the first bone 251 (e.g. femur) and includes a textured surface portion 215 that enables bone growth of the first bone 251 to become more fully attached to the first member 210. As shown in FIG. 4, the second member 220 is coupled to the second bone 253 (e.g. pelvis bone) using one or more screws 225 or other fastening devices.

In some embodiments, the second member 220 of the implantable hip joint 200 includes a cup portion 222 that is attachable to the second bone 253, and a liner portion 224 that is relatively more flexible that is disposed between the cup portion 222 and the ball portion 214 of the first member 210. In some embodiments, the liner portion 224 may be a resilient, flexible polymeric material (e.g. polyethylene) that provides a low-friction, resilient interface between the ball portion 214 of the first member 210 and the cup portion 222 of the second member 220. Accordingly, the first and second members 210, 220 may be operatively coupled with the ball portion 214 of the first member 210 fittingly received into the liner portion 224 of the second member 220, and the liner portion 224 coupled to the cup portion 222, enabling the first member 210 to operatively move (e.g. rotate, pivot) with respect to the second member 220 to form a moveable hip joint.

In some embodiments, the implantable hip joint 200 includes a heating system 230 that includes a main module 232 operatively coupled to the first member 210. For example, as shown in FIGS. 5-7, in some embodiments, the main module 232 is disposed within a recess 233 formed within the first member 210, and is enclosed by a cover member 235 that fittingly engages and seals the main module 232 into the recess 233 to secure and protect the main module 232.

Figure 8:
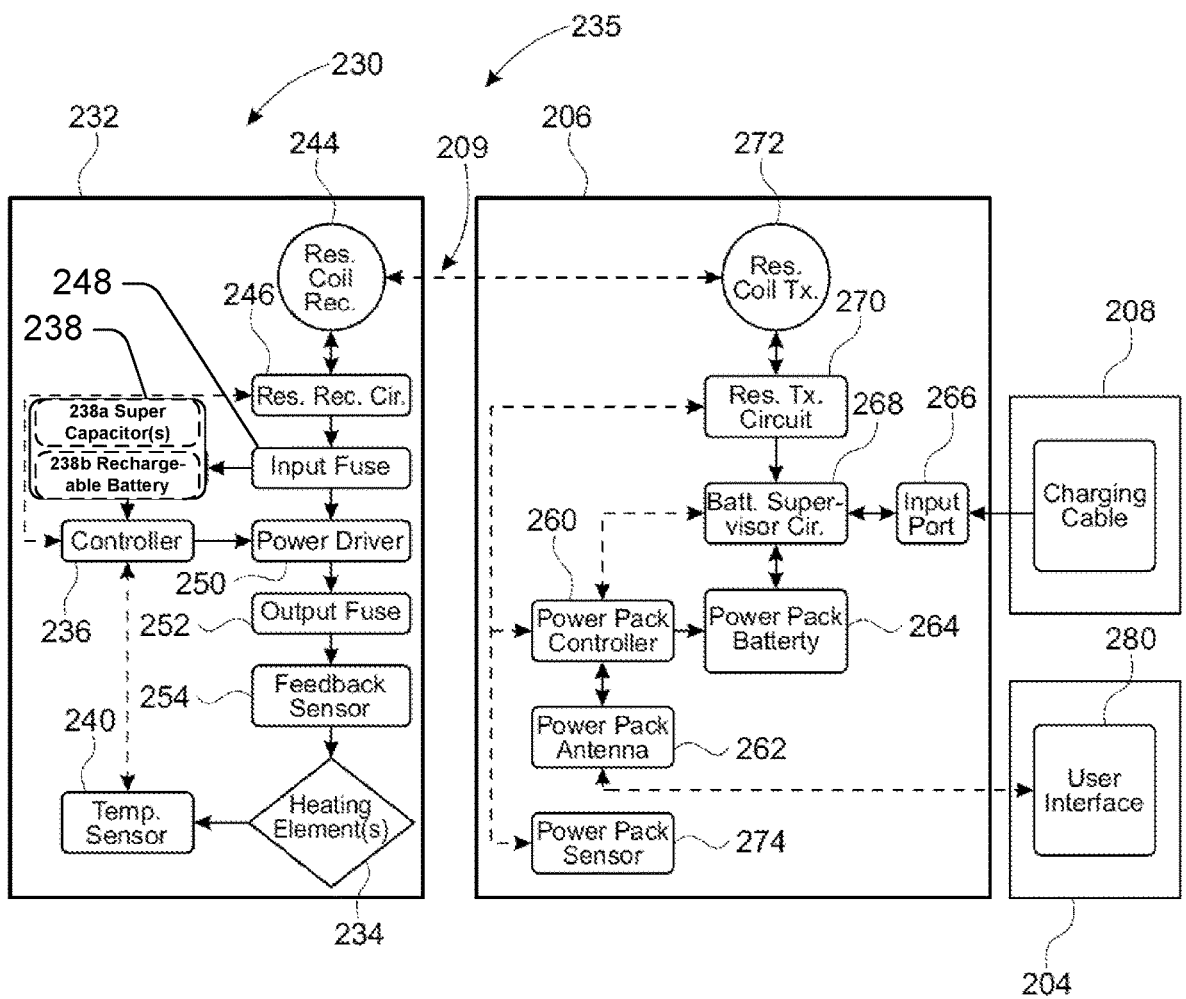
FIG. 8 is a schematic view of electrical components the system 200 of FIG. 3 in accordance with an example embodiment.
Figure 9:
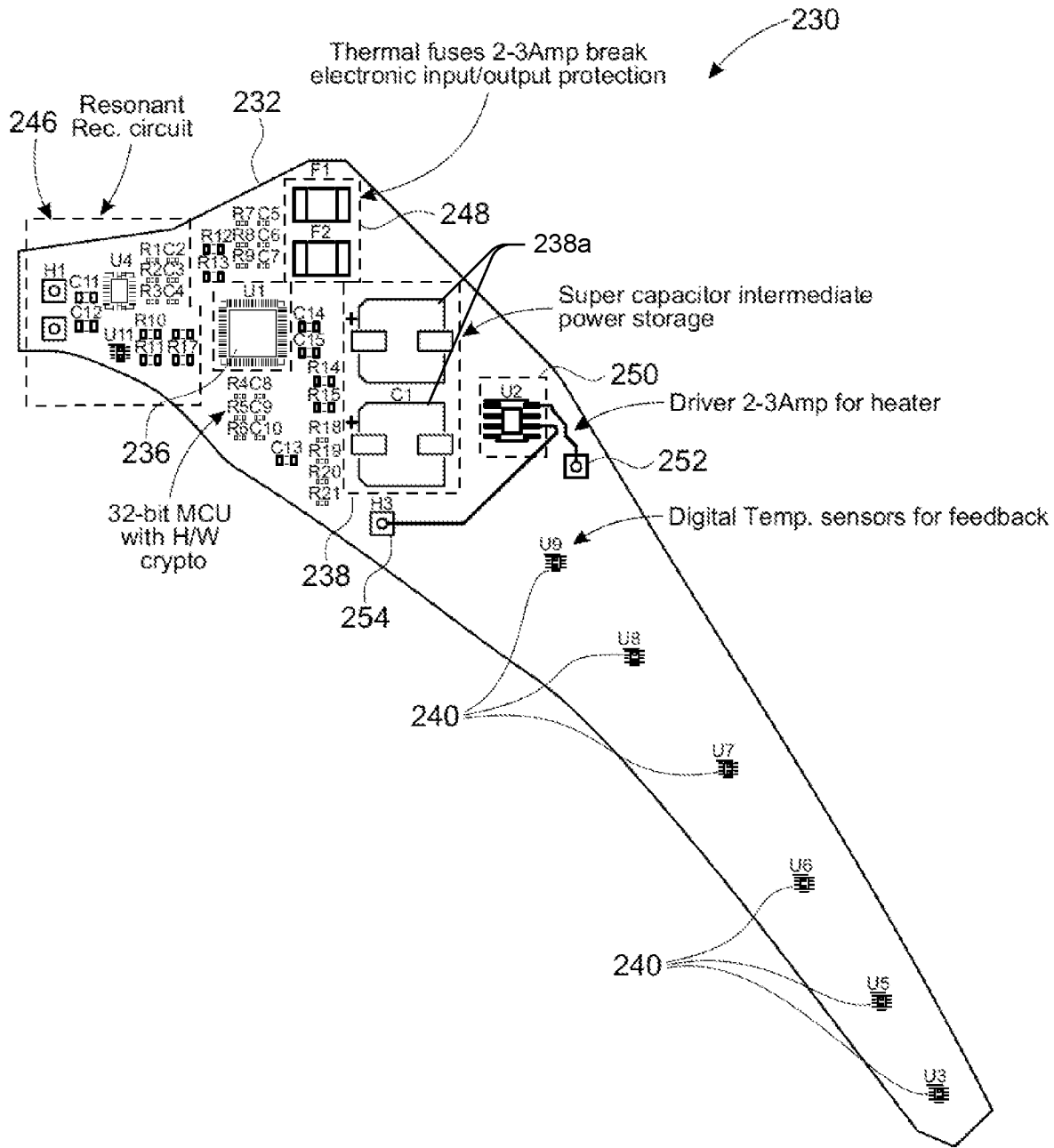
FIG. 9 is an elevational view of a heating system of the implantable hip joint of FIG. 3 in accordance with an example embodiment.
Figure 10:
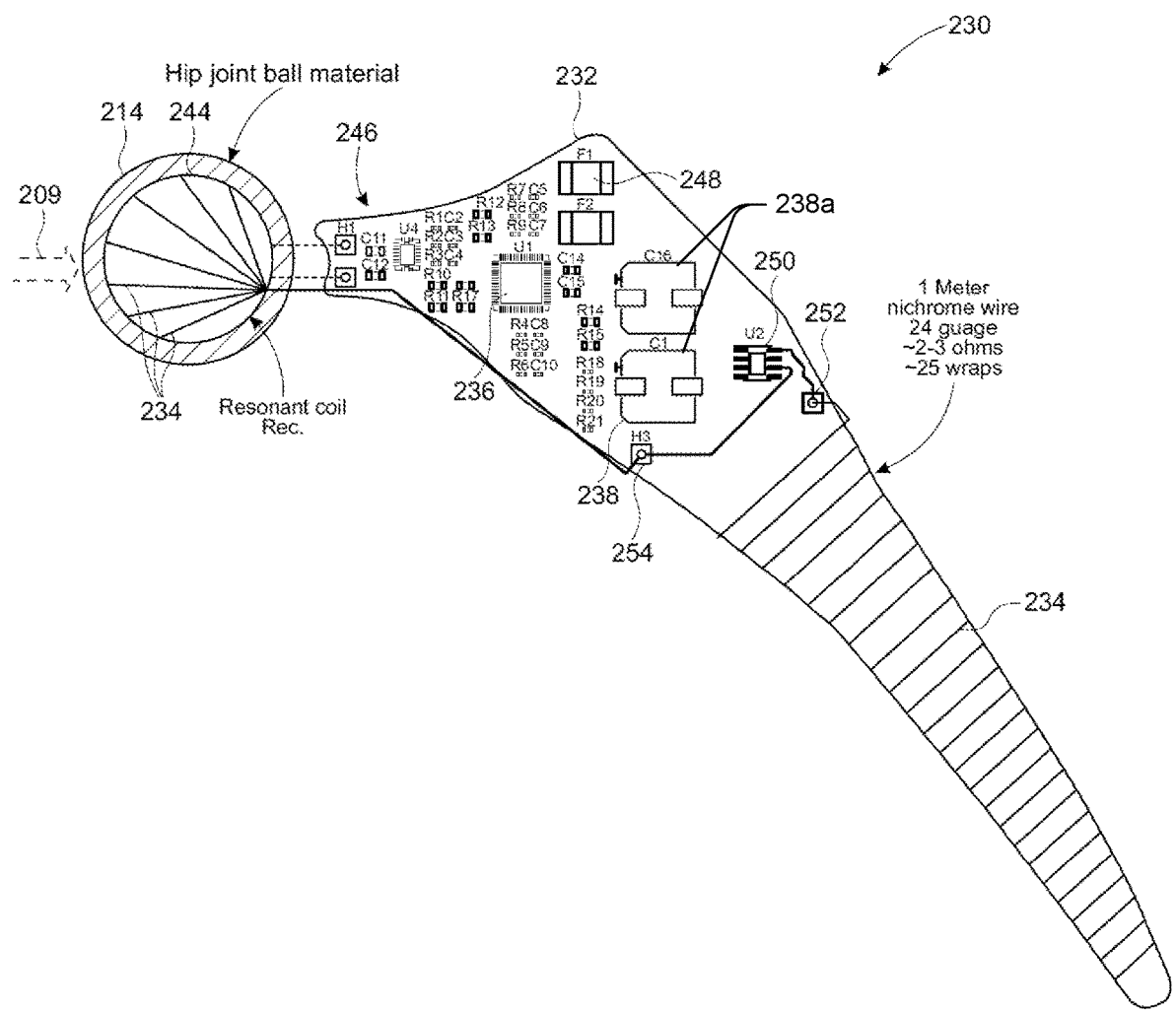
FIG. 10 is another elevational view of the heating system of the implantable hip joint of FIG. 3 in accordance with an example embodiment.

FIG. 8 is a schematic view of various components the system 200 of FIG. 3, including the heating system 230 of the implantable hip joint 202. FIGS. 9 and 10 are elevational views of the heating system 230 of the implantable hip joint 202 of FIG. 3. In some embodiments, the main module 232 is operatively coupled to heating elements 234 that are distributed over one or more portions of the first member 210. For example, as best shown in FIG. 10, in some embodiments, a first one of the heating elements 234 may be distributed over the stem portion 212 of the first member 210, and a second one of the heating elements 234 may distributed within the ball portion 214 of the first member 210. In some embodiments, the heating elements 234 may include a wire that warms and provides heat when an electrical current is passed through the wire. In some particular embodiments, the heating elements 234 may include a twenty-four gauge nichrome wire having approximately 2-3 ohm resistance, however, other suitable wires having other gauges and resistances may be employed. It will be appreciated that nichrome wires are extensively used in medical devices because of their robustness and thermal control properties. Although the heating elements 234 are shown in FIG. 10 as being wrapped or wound around the stem portion 212 and located within the ball portion 214 of the first member 210, in alternate embodiments, other heating elements 234 may be added, or the heating elements 234 may be extended, to provide heating to other portions of the first member 210, or to provide heating to one or more portions of the second member 220 (e.g. the cup portion 222).

In the embodiment shown in FIGS. 8-10, the main module 232 of the heating system 230 includes a controller 236 operatively coupled to a power supply 238. In some embodiments, the controller 236 of the implantable hip joint 202 may be equipped with hardware encryption peripherals to allow secure control and local patient data protection. In some embodiments, the power supply 238 may include a super capacitor 238a that stores electrical power that may be used to power the controller 236 and other components of the heating system 230 (e.g. heating elements 234). Similarly, in some embodiments, the power supply 238 may include a rechargeable battery 238b that stores electrical power that may be used to power the controller 236 and other components of the heating system 230 (e.g. heating elements 234). For example, in some embodiments, the heating power 209 may be typically provided to the heating system 230 of the implantable hip joint 202 via the wireless power link 235, which may provide for wireless high-power transfer thru the human tissue to the heater system 230. In some particular embodiments, for example, approximately 0-25 Watts of power can be delivered across the wireless power link 235. Moreover, in some embodiments, the wireless power link 235 can also provide a bidirectional communication link to send information wirelessly back to the power pack 206. And for intermediate storage in moments of wireless disconnection of the wireless power link 235, wherein the heating power 209 may be interrupted, in some embodiments, the power supply 238 (e.g. the super capacitor 238a or the rechargeable battery 238b, or both) may serve as an on-board power source to provide power the components of the heating system 230, such as the controller 236 and the heating elements 234. When the wireless power link 235 is properly established and providing the heating power 209 in a stable fashion, the heating system 230 can revert to using the heating power 209 to heat the heating elements 234 rather than the on-board power from the power supply 238 (e.g. super capacitor 238a, rechargeable battery 238b, or both).

The controller 236 may also coupled to one or more temperature sensors 240 (e.g. digital temperature sensors) that are configured to monitor a temperature of one or more components of the heating system 230, including the heating elements 234. For example, as shown in FIG. 9, the heating system 230 includes a plurality of temperature sensors 240 spaced apart along the stem portion 212 proximate several sections of the heating element 234. In some embodiments, the plurality of temperature sensors 240 may provide redundancy and temperature gradient information along the heating elements 234.

As noted above, in some embodiments, the power supply 238 may be a rechargeable power supply, such as a capacitor. In the embodiment shown in FIGS. 8-10, the main module 232 includes a resonant coil receiver 244 that is configured to wirelessly receive the heating power 209 from the power pack 206, and a resonant receiving circuit 246 coupled to the resonant coil receiver 244. In some embodiments, the resonant coil receiver 244 may be disposed within the ball portion 214 of the first member 210 as shown in FIG. 10. It will be appreciated that in some embodiments, the heating power 209 received by the resonant coil receiver 244 may be used to provide power to perform various functions of the heating system 230, such as to provide power to the heating element 234 to heat the one or more portions of the implantable hip joint 202, as well as to recharge the power supply 238, or to provide power to any other components of the heating system 230.

In some embodiments, during charging operations, the controller 236 may monitor a charge level of the power supply 238 and one or more operating conditions of the resonant receiving circuit 246, and may provide control signals that enable (or discontinue) charging of the power supply 238 by the resonant receiving circuit 246. In addition, in some embodiments, an input fuse 248 (e.g. a thermal fuse) may be disposed between the resonant receiving circuit 246 and the power supply 238 may open to discontinue one or more operations of the heating system 230, such as recharging of the power supply 238 by the resonant receiving circuit 246, in the event that an undesirable operating condition is detected (e.g. a short or other non-optimal condition).

As further shown in FIGS. 8-10, in some embodiments, the controller 236 is coupled to a power driver 250 that drives power from the power supply 238 to the heating element 234. In some embodiments, an output fuse 252 (e.g. thermal fuse) is disposed between the power driver 250 and the heating element 234 and is configured to open to discontinue one or more operations of the heating system 230, such as the powering of the heating element 234 by the power driver 250 in the event that an undesirable operating condition is detected. Similarly, in some embodiments, a feedback sensor 254 may monitor one or more operating conditions (e.g. voltage, current) as power is provided by the power driver 250 to the heating element 234. Outputs from the feedback sensor 254 may be provided to the controller 236 to enable the controller 236 to monitor operating conditions as the power is provided to the heating element 234. More specifically, in some embodiments, the feedback sensor 254 may monitor the power delivered to the heating element 234 and to provide that information to the controller 236 for controlling operation of the heating system 230.

As noted above, the controller 236 may control the power driver 250 to provide power from the power supply 238 to the heating element 234. Alternately, in some embodiments, the power driver 250 may be controlled by the controller 236 to provide power from the resonant receiving circuit 246 to the heating element 234.

It will be appreciated that several aspects of the implantable hip joint 202 are intended to enhance safe operations of the implantable hip joint 202. For example, in some embodiments, the controller 236 may be properly programmed to maintain safe operations of the heating system 230, such as by programming the controller 236 (e.g. software, programmable hardware, etc.) to limit the possibility of a large power draw, or to halt heating functionalities when certain limits or conditions are determined. In addition, in some embodiments, the input fuse 248 and the output fuse 252 may be configured to control heating by the heating system 230, as well as to protect the other components of the heating system 230, and to prevent a large power draw by the heating system 230 to maintain or enhance patient safety. In some embodiments, the input and output fuses 248, 252 may be thermal fuses and may have a suitable reset period (e.g. several seconds, several minutes, etc.) to ensure sufficient time for one or more components of the heating system 230 to reset or restart to correct operating conditions, thereby maintaining or enhancing safety.

Figure 11:
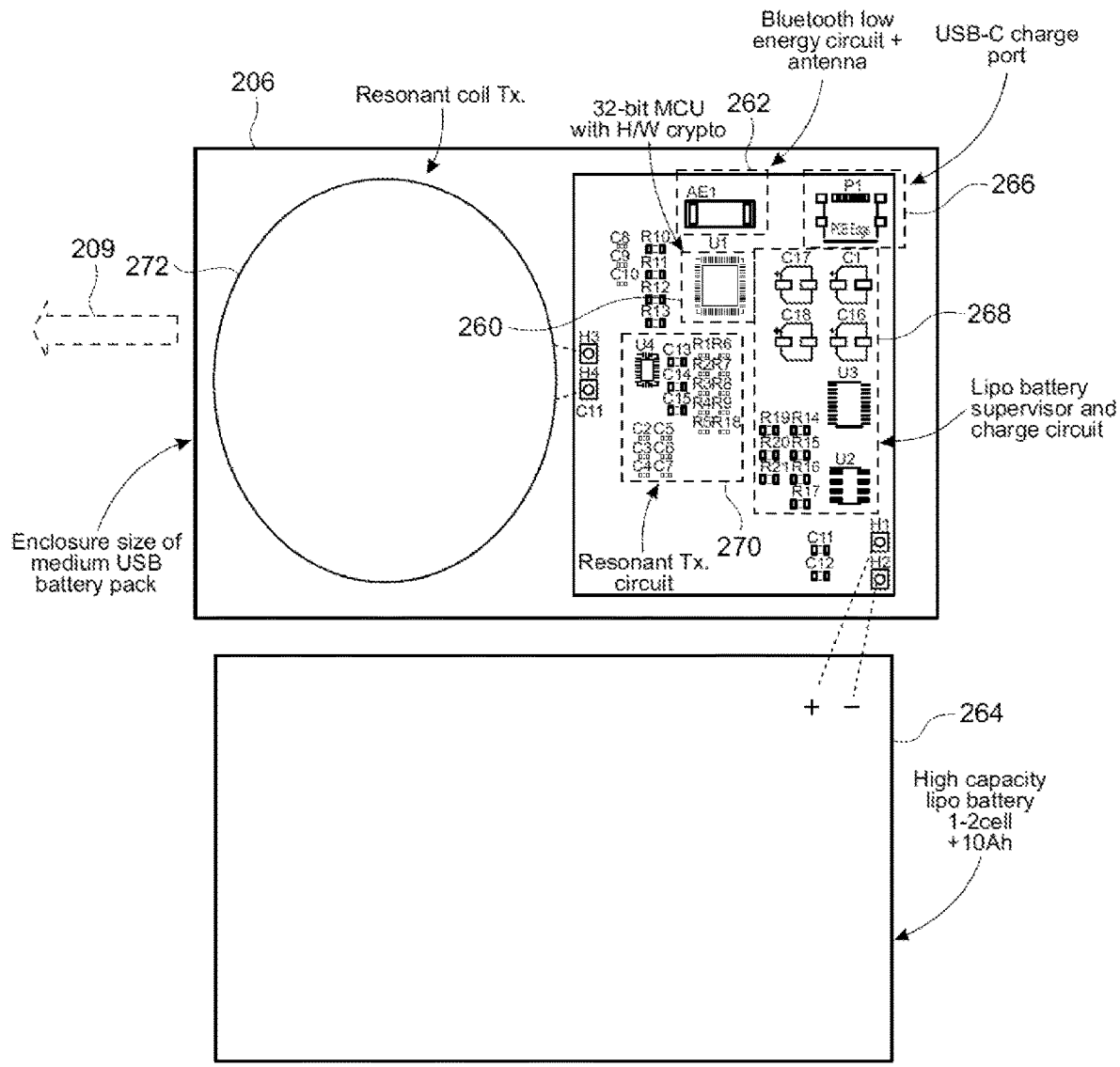
FIG. 11 is an elevational view of the power pack module of FIG. 3 in accordance with an example embodiment.

FIG. 11 is an elevational view of the power pack 206 of FIG. 3 in accordance with an example embodiment. As noted above, the power pack 206 may be configured to wirelessly deliver the heating power 209 to the implantable hip joint 202. In some embodiments, the power pack 206 includes a power pack controller 260 configured to control one or more operations of the power pack 206, and a power pack antenna 262 operatively coupled to the power pack controller 260. In some embodiments, the power pack controller 260 may be equipped with hardware encryption peripherals to allow secure control and local patient data protection. The power pack antenna 262 may be configured to communicate (e.g. transmit and receive) signals with the monitoring component 204, such as via a Bluetooth communication protocol. More specifically, in some embodiments, the power pack 206 communicates with the monitoring component 204 via the power pack antenna 262 using a Bluetooth LE 4.0 (and above) capability.

In some embodiments, the power pack controller 260 is operatively coupled to a power pack battery 264. For example, the power pack battery 264 may be a relatively high-capacity battery, such as a lithium-ion polymer (Lipo) battery or the like, capable of storing a relatively large amount of power (e.g. 10 Ah). Of course, in alternate embodiments, any other suitable type of battery may be used.

In the embodiment shown in FIG. 11, the power pack 206 further includes an input port 266 that is configured to be coupled to the charging component 208 to receive a charging power, and a battery supervisor circuit 268 that is coupled between the input port 266 and the power pack battery 264. For example, in some embodiments, the input port 266 may be a USB C port for easy engagement with a corresponding USB plug of the charging component 208. The battery supervisor circuit 268 may be configured to monitor the power pack battery 264 and to manage the power during charging operations to properly charge the power pack battery 264, and to provide correct power to the other components of the power pack 206.

In some embodiments, the battery supervisor circuit 268 is also coupled to a resonant transmitter circuit 270 that is, in turn, coupled to a resonant coil transmitter 272. The resonant transmitter circuit 270 may be configured to provide power from the power pack battery 264 to the resonant coil transmitter 272, and the resonant coil transmitter 272 may be configured to provide the heating power 209 to the resonant coil receiver 244 of the implantable hip joint 202.

It will be appreciated that the resonant coil transmitter 272 of the power pack 206, and the resonant coil receiver 244 of the implantable hip joint 202, provide the wireless power link 235 for wirelessly transferring power thru the human tissue to the implantable hip joint 202 in vivo within the patient. In some embodiments, up to approximately 25 Watts of power can be provided across the wireless power link 235 (i.e. resonant coil transmitter 272 and resonant coil receiver 244). In some embodiments, the wireless power link 235 may also be configured to provide bi-directional communication of signals to enable information to be transmitted through the wireless power link 235 between the implantable hip joint 202 and the power pack 206. In some embodiments, when a wireless power connection is established via the wireless power link 235, the controller 236 may control the resonant receiver circuit 246 to provide power directly from the resonant coil receiver 244 to the heating element 234.

In operation, the power pack controller 260 may control the transfer of power from the power pack battery 264 to the resonant transmitter circuit 270 and the resonant transmitter coil 272 (via the battery supervisor circuit 270). In some embodiments, the resonant transmitter circuit 270 may bidirectionally communicate with the resonant receiver circuit 246 via the wireless power link 235 during transfer of the heating power 209 for monitoring and command control to ensure that the heating power 209 is properly transferred from the power pack 206 to the implantable hip joint 202.

As further shown in FIG. 11, in some embodiments, the power pack 206 includes a power pack sensor 274 operatively coupled to the power pack controller 260. The power pack sensor 274 may be configured to detect one or more conditions that may be used by the power pack controller 260 or other components of the system 200 to determine whether to apply heat (or discontinue heating) to the implantable hip joint 202 using the heating system 230. For example, in some embodiments, the power pack sensor 274 may measure one or more of temperature, humidity, barometric pressure, time of day, activity level of the patient (e.g. number of steps, etc.) or any other possible conditions in the external environment proximate to the power pack 206. In a particular embodiment, the power pack sensor 274 measures both temperature and humidity and provides these measurements to the power pack controller 260.

In some embodiments, in response to the one or more conditions measured by the power pack sensor 274, the power pack controller 260 may automatically initiate transfer of the heating power 209 from the power pack 206 to the implantable hip joint 202 via the wireless power link 235.

Alternately, in some embodiments, in response to the one or more conditions measured by the power pack sensor 274, the power pack controller 260 may transmit a query to the monitoring component 204 via the power pack antenna 262 to seek authorization from the person whether to apply heat (or discontinue heating) to the implantable hip joint 202 using the heating system 230.

Referring again to FIG. 8, in some embodiments, the monitoring component 204 includes a user interface 280. For example, in some embodiments, where the monitoring component 204 is a handheld device such as a cellular telephone or other commercially-available device, the user interface 280 may be configured as a software application that runs on the monitoring component 204, displaying information about the system 200 to the person on the built-in display of the monitoring component 204 and receiving inputs from the person using a keyboard, microphone, or other input/output components of the monitoring component 204. Accordingly, in some embodiments, the monitoring component 204 may monitor information provided by the power pack 206 and the implantable hip joint 202, display the information to the person via the user interface 280, and may enable the person to provide inputs to the system 200 (e.g. to the power pack 206, to the implantable hip joint 202, etc.) via the user interface 280 to control various aspects of the system 200, including whether to apply heat (or discontinue heating) to the implantable hip joint 202 using the heating system 230. In some embodiments, the monitoring component 204 may be configured to communicate with the power pack 206 and/or with the implantable hip joint 202 using encrypted communications to provide enhanced security, control, and data protection.

In some embodiments, the monitoring component 204 includes a smart telephone (e.g. commercially-available Android phone, iPhone, etc.), and the user interface 280 includes a smartphone mobile medical application (MMA), that is configured to control, manage, communicate, and display relevant data from one or more components of the system 200 (e.g. implantable heat joint 202, power pack 206, etc.). Using wireless communication technologies such as Bluetooth, Wi-Fi, or cellular networks, the MMA discovers the implantable hip joint 202, authenticates the connection, and establishes a secure link with the smart technology implanted in the implantable hip joint 202. The MMA and display of the smart phone may allow the user to monitor exterior temperature, humidity, interior joint implant material temperature, the user's body temperature, and any other conditions while the implantable hip joint 202 warms up during operation of the heating system 230, and cools down as the heating system 230 is discontinued.

It will be appreciated that the monitoring component 204 may detect and monitor changes in one or more conditions (e.g. temperature, humidity, etc.), using inputs from any of the sensors within the power pack 206 (e.g. power pack sensor 274) or within the implantable hip joint 202 (e.g. temperature sensor 240), or using inputs from any other suitable source (e.g. received via a weather service via a Wi-fi communication), and may adjust operating conditions of the system 200 to reach a warmer comfort level (or to discontinue heating). In some embodiments, the user may be notified via the user interface 280 of one or more specific events or conditions detected by the implantable hip joint 202 or by the power pack 206 and on what actions to take or have already been taken.

In some embodiments, the monitoring component 204 may be configured to track the power pack 206 supplying the heating power 209 to the implantable hip joint 202, and when a recharge of the power pack 206 (or the implantable hip joint 202) is required. In some embodiments, when the power supply 238 of the implantable hip joint 202 is strong enough for sustained operations of the heating system 230, the architecture of the system 200 is suitable for use with such implanted battery power. The level of the power supply 238 of the implantable hip joint 202 may be monitored by the monitoring component 204, and recharging of the power supply 238 of the implantable hip joint 202 may be performed using the wireless power link 235 technology currently supplying external power from the power pack 206 (or directly from the charging component 208). Accordingly, as noted above, in some embodiments, the heating power 209 may be typically provided to the heating system 230 of the implantable hip joint 202 via the wireless power link 235, which may provide for wireless high-power transfer thru the human tissue to the heater system 230. In the event that the heating power 209 via the wireless power link 235 becomes interrupted or degraded, the power supply 238 (e.g. the super capacitor 238a or the rechargeable battery 238b, or both) may serve as an on-board power source to provide power the components of the heating system 230, such as the controller 236 and the heating elements 234. And when the wireless power link 235 is properly established and providing the heating power 209, the heating system 230 can revert to using the heating power 209 to heat the heating elements 234 rather than the on-board power from the power supply 238 (e.g. super capacitor 238a, rechargeable battery 238b, or both).

In some embodiments, the MMA may be designed for users to access settings and status of the system 200, allowing users to manage the system 200 without providing specific treatment suggestions. In addition, the MMA may display automatic simple tasks, and if the user uploads the data to an encrypted cloud-based health account, that data could be made available to the user's health care provider.

Referring again to FIG. 8, in some embodiments, the charging component 208 may provide charging power from a power source to the power pack 206 via the input port 266. For example, in some embodiments, the charging component 208 may include a charging cable 282 that connects a relatively stationary power source (e.g. a wall outlet, generator, etc.) to the input port 266 of the power pack 206. More specifically, in some embodiments, the charging cable 282 of the charging component 208 may include a USB C charger, or other suitable commercially-available charging cable.

It will be appreciated that embodiments of implantable joints in accordance with the present disclosure may provide substantial advantages over prior art devices. For example, because implantable joints (e.g. implantable hip joints 100, 200) in accordance with the present disclosure include a heating system (e.g. heating system 130, 230) that is configured to warm one or more portions of the implantable joint, persons who may be negatively affected by various conditions such as temperature, humidity, or other environmental or personal conditions may control the implantable joint to apply heating to the implantable joint. Providing heat to the implantable joint may advantageously decrease pain and discomfort that would otherwise be experienced by the patient. In some cases, providing heat may also stimulate blood flow proximate to the implantable joint, which may in some cases along with provide warming of local tissues, such as bone, the heat replaces the body's natural warming mechanism of blood flowing through bone marrow, in the interior of bone, which is now gone and has been replaced by man-made plastic, ceramic and metals. This manufactured heat from the heating system of the implantable joint may penetrate the interior of the joint replacement, and may supplement the body's heating of the joint material which up until now has only been warmed by the blood circulating around the outside of the replacement material. This additional heat may also provide improved comfort to the patient. In addition, in some embodiments, the implantable joint having a heating system may improve temperature regulation of the implantable joint that is otherwise deficient or missing from prior art devices, thereby improving comfort and overall satisfaction of the patient.

Although the description above has thus far involved implantable hip joints, it will be appreciated that the present disclosure is not limited to implantable hip joints, and that the above-described systems and methods may be equally applicable to other implantable joints. For example, in other embodiments in accordance with the present disclosure, the implantable joint may be a knee joint, a shoulder joint, or any other artificial joint disposed within the human body.

Figure 12:
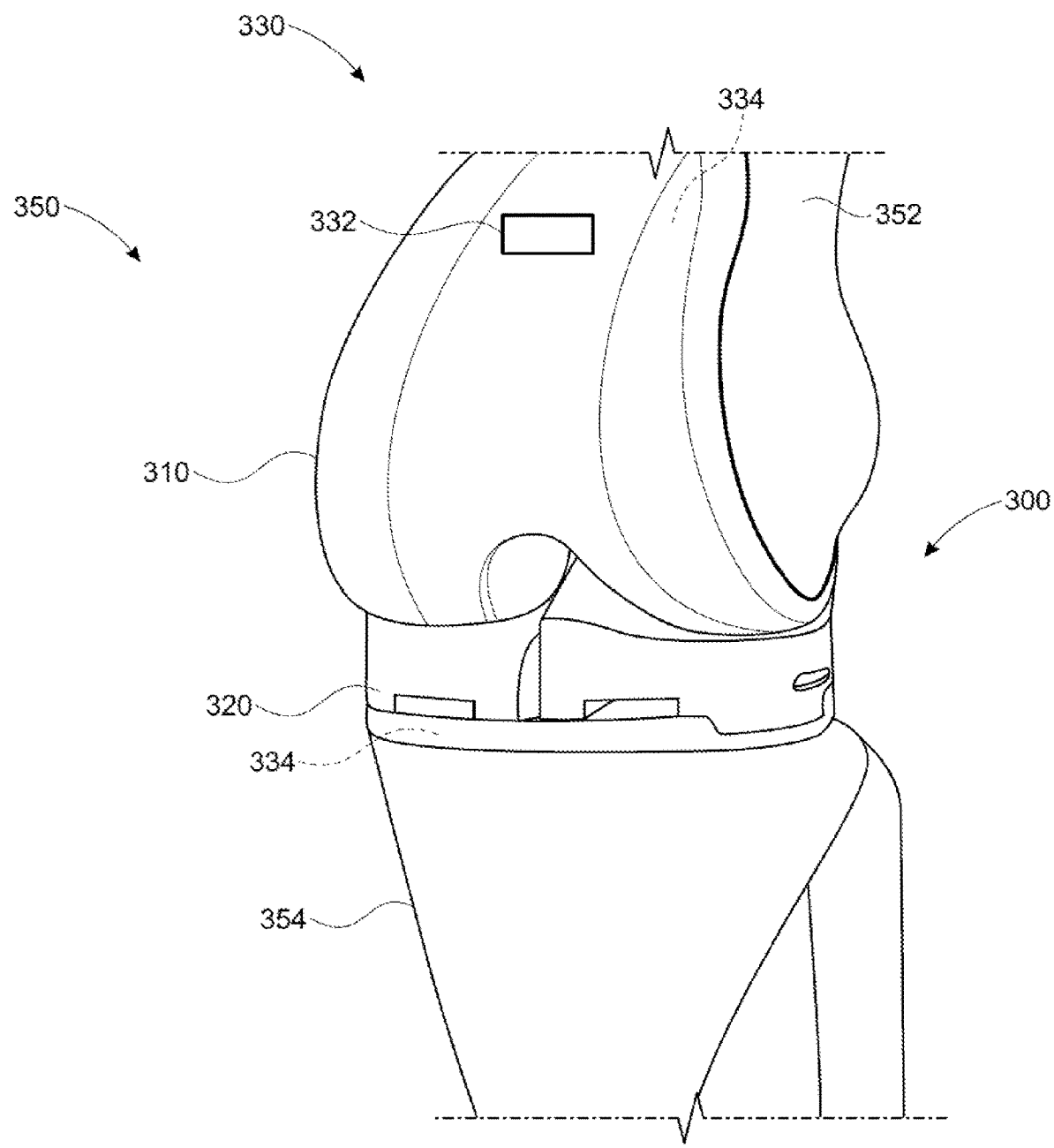
FIG. 12 is a perspective view of an implantable knee joint located in a representative environment in accordance with an example embodiment.

For example, FIG. 12 is a perspective view of an implantable knee joint 300 located in a representative environment 350 in accordance with an example embodiment. In some embodiments, the implantable knee joint 300 includes a first member 310 configured to be coupled to a first bone 352 and a second member 320 configured to be coupled to a second bone 354. More specifically, as shown in FIG. 12, the first bone 352 may be a femur, and the second bone 154 may be a portion a tibia. As noted above, the first and second members 310, 320 may be coupled to the first and second bones 352, 354 by cement, press fit, fasteners (e.g. screws, pins, etc.), or any other suitable manner. Similarly, the first and second members 310, 320 may be configured with porosity, apertures, surface roughness, or other similar features to help secure the first and second members 310, 320 to the first and second bones 352, 354, respectively. In some embodiments, the first and second members 310, 320 are operatively coupled to form a moveable knee joint of a human being.

With continued reference to FIG. 12, the implantable knee joint 300 further includes a heating system 330 operatively coupled to at least one of the first and second members 310, 320 and configured to controllably heat at least a portion of the first and second members 310, 320. In some embodiments, the heating system 330 includes a main module 332 that is operatively coupled to one or more heating elements 334. In some embodiments, the heating elements 334 may be distributed over (or within) various surfaces of the first and second members 310, 320 (e.g. see FIGS. 1, 10), and may controllably provide heating to some or all of the implantable knee joint 300 as described more fully above.

In some embodiments, the main module 332 may be configured substantially similar to the embodiments of main modules 132, 232 as described above with reference to FIGS. 1-11, and for the sake of brevity, will not be repeated herein. In general, the main module 332 may be configured to receive one or more inputs indicative of one or more environmental conditions, and to cause the heating elements 334 to provide warmth to one or more portions of the implantable knee joint 300 and/or the surrounding bones 352, 354 and tissues of the person's body. Accordingly, the above-noted advantages of implantable joints having a heating system may be achieved in embodiments of implantable knee joints (e.g. implantable knee joint 300).

Figure 13:
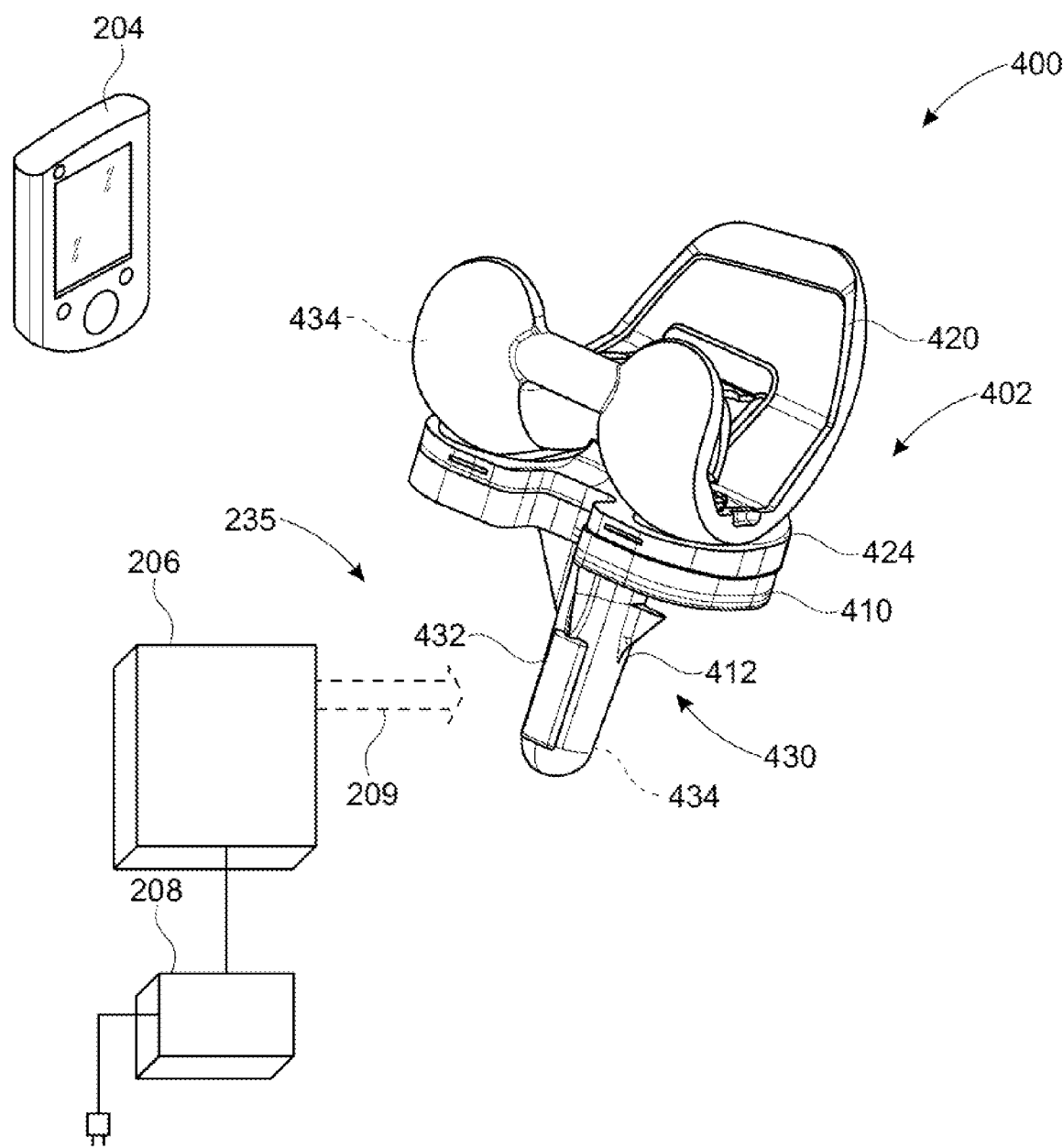
FIG. 13 is a perspective view of a system that includes an implantable knee joint in accordance with another example embodiment.

Similarly, FIG. 13 is a perspective view of a system 400 that includes an implantable knee joint 402 in accordance with another example embodiment. In the embodiment shown in FIG. 13, the system 400 includes an implantable knee joint 402, a monitoring component 204, a power pack 206, and a charging component 208. It will be appreciated that the monitoring component 204, the power pack 206, and the charging component 208 have been described in detail above, and may operate is substantially similar manner in the system 400 that includes the implantable knee joint 402 as shown in FIG. 13.

In some embodiments, the implantable knee joint 402 includes a first member 410 configured to be coupled to a first bone (e.g. a tibia) and a second member 420 configured to be coupled to a second bone (e.g. a femur). In some embodiments, the first member 410 includes a stem portion 212 configured to be inserted into the first bone (e.g. tibia). In some embodiments, the implantable knee joint 402 further includes a liner portion 424 disposed between the first member 410 and the second member 420. In some embodiments, the liner portion 424 is a resilient, flexible polymeric material (e.g. polyethylene) that provides a low-friction, resilient interface between the first member 410 and the second member 420. Accordingly, the first and second members 410, 420 and the liner portion 424 are operatively coupled to enable the first member 410 to operatively move (e.g. rotate, pivot) with respect to the second member 420 to form a moveable knee joint.

In some embodiments, the implantable knee joint 400 includes a heating system 430 that includes a main module 432 operatively coupled to one or more heating elements 434 that are distributed over (or within) one or more portions of the first member 410 and the second member 420. For example, as best shown in FIG. 10, in some embodiments, at least one heating element 434 may be distributed over the stem portion 412 of the first member 410. Similarly, as shown in FIG. 1, at least one heating element 434 may be distributed over the second member 420.

In brief, in some embodiments, the monitoring component 204 may have various communication and input/output functionalities that enable a user to monitor and provide inputs and commands to other components of the system 400, including the components of the implantable knee joint 402 and the power pack 206. In some embodiments, the power pack 206 may be a device that stores power and that provides the heating power 209 to the implantable knee joint 402 as needed by the wireless power link 235 between the implantable knee joint 402 and the power pack 206. In addition, in some embodiments, the charging component 208 may be coupled to the power pack 206 and to a power supply (e.g. a wall outlet, a generator, etc.) to recharge the power pack 206 after use. And in some embodiments, the monitoring component 204 may includes the user interface 280 (FIG. 8), and may be configured to monitor information provided by the power pack 206 and the implantable knee joint 402, display the information to the person via the user interface 280, and enable the person to provide inputs to the system 400 (e.g. to the power pack 206, to the implantable knee joint 402, etc.) via the user interface 280 to control various aspects of the system 400, including whether to apply heat (or discontinue heating) to the implantable knee joint 402 using the heating system 430. Accordingly, the above-noted advantages of implantable joints having a heating system may be achieved in embodiments of systems (e.g. system 400) that include an implantable knee joint (e.g. implantable knee joint 402), and one or more of a power pack 206, a monitoring component 204, and a charging component 208.

Figure 14:
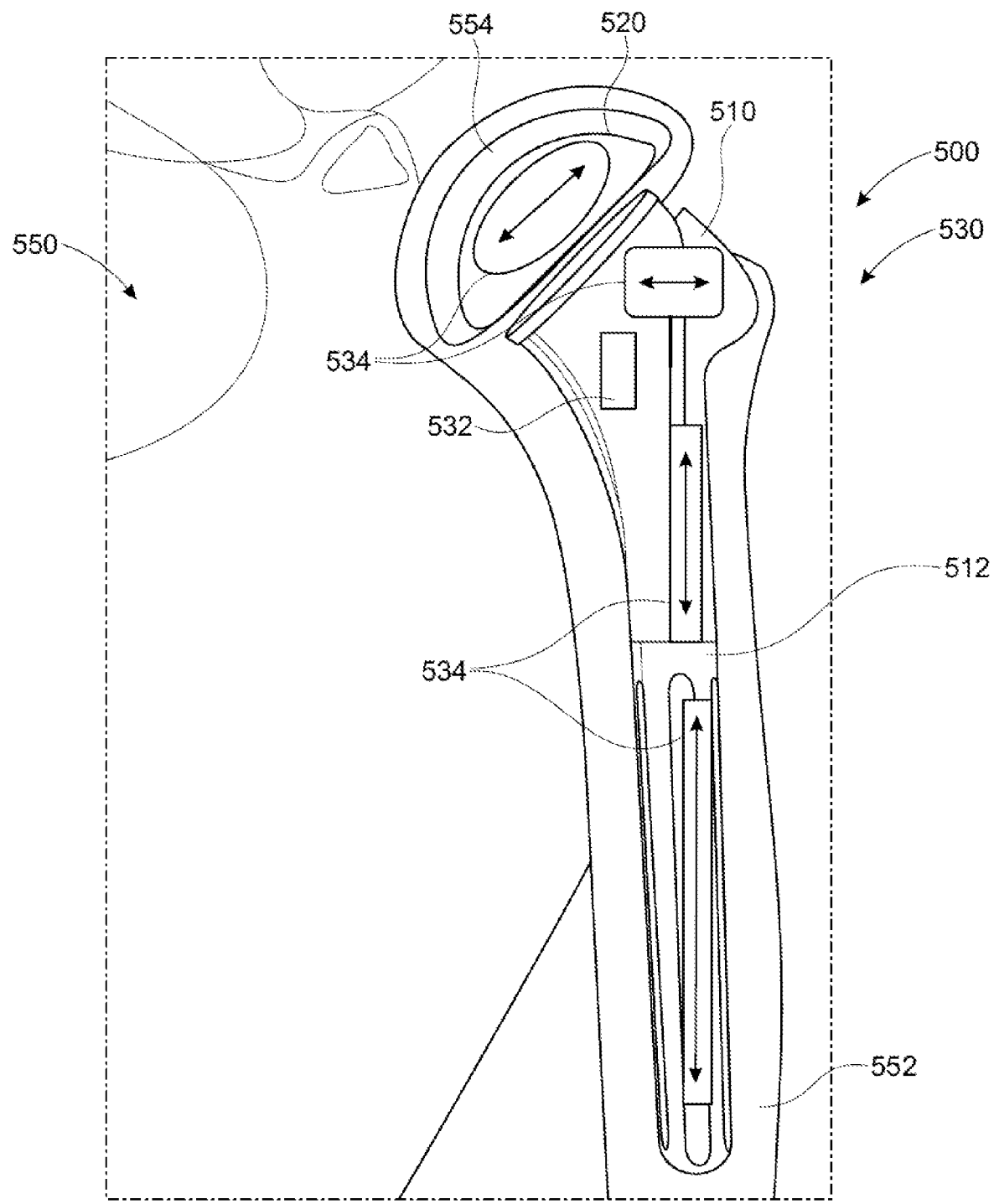
FIG. 14 is a perspective view of an implantable shoulder joint located in a representative environment in accordance with an example embodiment.

In addition, FIG. 14 is a perspective view of an implantable shoulder joint 500 located in a representative environment 550 in accordance with another example embodiment. In some embodiments, the implantable shoulder joint 500 includes a first member 510 configured to be coupled to a first bone 552 and a second member 520 configured to be coupled to a second bone 554. More specifically, as shown in FIG. 14, the first bone 552 may be a humerus, and the second bone 554 may be a portion a scapula. In some embodiments, the first and second members 510, 520 are operatively coupled to form a moveable shoulder joint of a human being.

With continued reference to FIG. 14, the implantable shoulder joint 500 further includes a heating system 530 operatively coupled to at least one of the first and second members 510, 520 and configured to controllably heat at least a portion of the first and second members 510, 520. In some embodiments, the heating system 530 includes a main module 532 that is operatively coupled to one or more heating elements 534. In some embodiments, the heating elements 534 may be distributed over (or within) various surfaces of the first and second members 510, 520, and may controllably provide heating to some or all of the implantable shoulder joint 500.

In some embodiments, the main module 532 may be configured substantially similar to the embodiments of main modules 132, 232 as described above with reference to FIGS. 1-11, and for the sake of brevity, will not be repeated herein. In general, the main module 532 may be configured to receive one or more inputs indicative of one or more environmental conditions, and to cause the heating elements 534 to provide warmth to one or more portions of the implantable shoulder joint 500 and/or the surrounding bones 552, 554 and tissues of the person's body. Accordingly, the above-noted advantages of implantable joints having a heating system may be achieved in embodiments of implantable shoulder joints (e.g. implantable shoulder joint 500).

Figure 15:
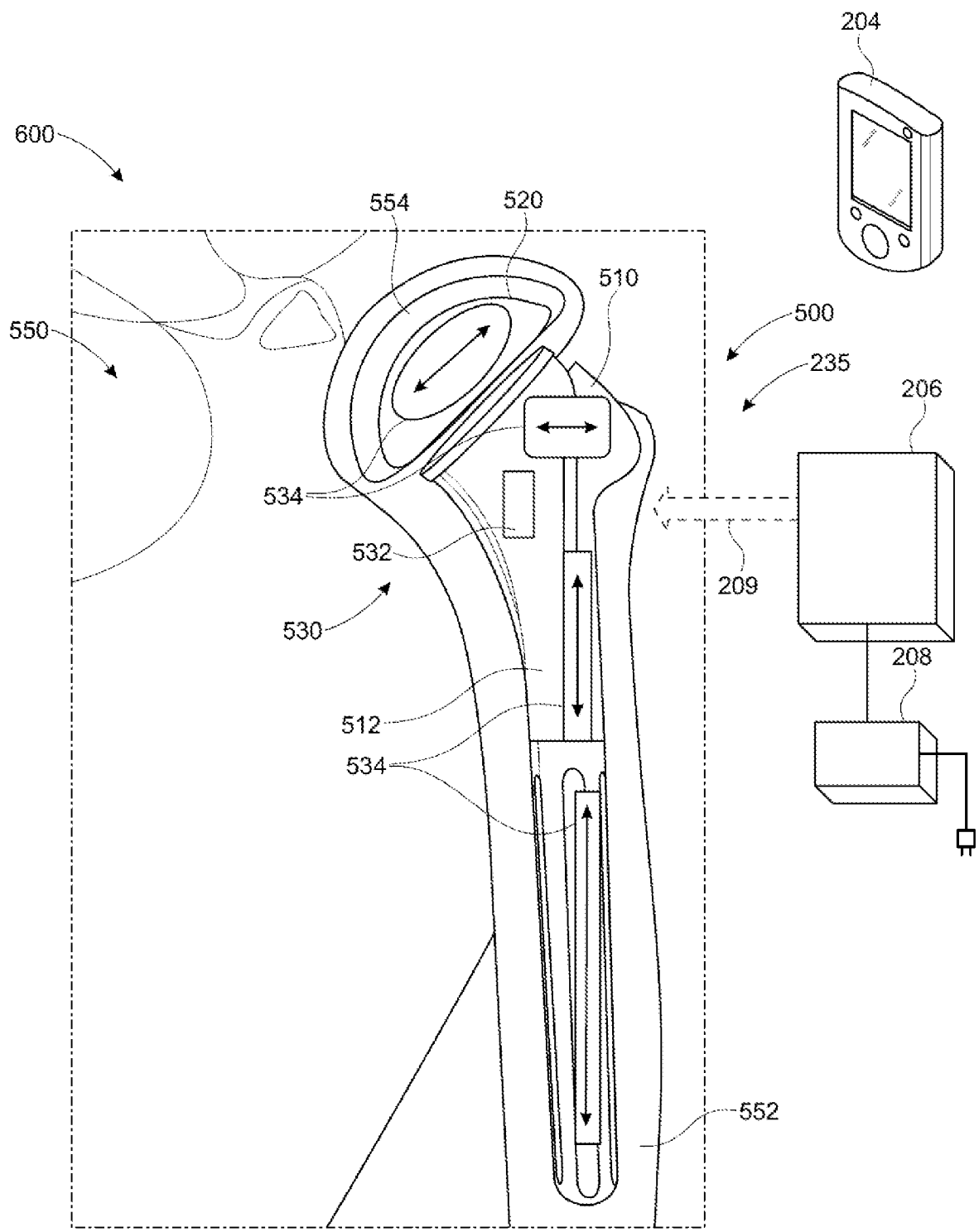
FIG. 15 is a perspective view of a system that includes an implantable shoulder joint in accordance with another example embodiment.

FIG. 15 is a perspective view of a system 600 that includes an implantable shoulder joint 500 in accordance with another example embodiment. In the embodiment shown in FIG. 15, the system 600 includes an implantable shoulder joint 500, a monitoring component 204, a power pack 206, and a charging component 208. It will be appreciated that the monitoring component 204, the power pack 206, and the charging component 208 have been described in detail above, and may operate is substantially similar manner in the system 600 that includes the implantable shoulder joint 500 as shown in FIG. 15.

In brief, in some embodiments, the monitoring component 204 may have various communication and input/output functionalities that enable a user to monitor and provide inputs and commands to other components of the system 600, including the components of the implantable shoulder joint 500 and the power pack 206. In some embodiments, the heating system 530 of the implantable shoulder joint 500 includes the above-described components necessary to form the wireless power link 235 between the main module 532 and the power pack 206. Thus, in some embodiments, the power pack 206 stores power and provides the heating power 209 to the implantable shoulder joint 500 via the wireless power link 235 between the implantable shoulder joint 500 and the power pack 206. In addition, in some embodiments, the charging component 208 may be coupled to the power pack 206 and to a power supply (e.g. a wall outlet, a generator, etc.) to recharge the power pack 206 after use. And in some embodiments, the monitoring component 204 may includes the user interface 280 (FIG. 8), and may be configured to monitor information provided by the power pack 206 and the implantable shoulder joint 500, display the information to the person via the user interface 280, and enable the person to provide inputs to the system 400 (e.g. to the power pack 206, to the implantable shoulder joint 500, etc.) via the user interface 280 to control various aspects of the system 600, including whether to apply heat (or discontinue heating) to the implantable shoulder joint 500 using the heating system 530. Accordingly, the above-noted advantages of implantable joints having a heating system may be achieved in embodiments of systems (e.g. system 600) that include an implantable shoulder joint (e.g. implantable shoulder joint 500), and one or more of a power pack 206, a monitoring component 204, and a charging component 208.

In general, a variety of battery systems are known for implantable medical devices. For example, in some implementations, a battery includes lithium metal anodes with cathode systems including iodine, manganese oxide, carbon monofluoride, silver vanadium oxide and hybrid cathodes. Alternately, secondary lithium-ion batteries may be used for medical applications where the batteries are charged while remaining implanted. Generally, batteries for use in implantable devices may desirably exhibit high safety, reliability and volumetric energy density, long service life, and state of discharge indication.

For example, in some implementations, long-life batteries that harvest energy from the nuclear decay of isotopes may be used. Some batteries could last decades for implantable medical devices.

A particular implementation of battery is known as a betavoltaic battery that contains layers of silicon carbide and metal foil embedded with the radioactive isotope tritium. When high-energy electrons emitted by the decay of tritium hit the siliconcarbide, it produces an electrical current that exits the cell through the metal pins. Such batteries are designed to last 25 years.

Other batteries are powered by the decay of a hydrogen isotope called tritium into high-energy electrons. While solar cells use semiconductors such as silicon to capture energy from the photons in sunlight, betavoltaic cells use a semiconductor to capture the energy in electrons produced during the nuclear decay of isotopes. This type of nuclear decay is called "beta decay," for the high-energy electrons, called beta particles, that it produces. The lifetimes of betavoltaic devices depend on the half-lives, ranging from a few years to 100 years, of the radioisotopes that power them. To make a battery that lasts 25 years from tritium, which has a half-life of 12.3 years, a battery may include twice as much tritium as is initially required. These devices can withstand much harsher conditions than chemical batteries. Thus, betavoltaics are attractive as a power source for medical implants a. For medical implants, tritium is safe. Besides the beta particle, other products of tritium's decay are an antineutrino and an isotope of helium that is not radioactive. While tritium has a half-life of only 12.3 years, one of its chief advantages, besides safety, is that it can be secured cheaply. Longer half-life isotopes such as nickel-63 may also be employed. In addition, Li-Ion batteries are available that can last 12 to 25 years currently and can be recharged.

In some implementations, devices in accordance with the present disclosure may draw energy directly from the patient's body into which they are implanted. For example, a battery may be implemented as a biological supercapacitor, which operates using charged particles (or ions) from fluids in the patient's body. In some implementations, such a biological supercapacitor battery may include an energy harvester that uses electrolytes from biological fluids (e.g. blood, blood serum, urine, etc.), and converts heat and motion from the human body into electricity. That electricity may in turn be captured by the biological supercapacitor battery to provide power to the implantable device. In some implementations, the biological supercapacitor may include a carbon nanomaterial called graphene layered with modified human proteins as an electrode, a conductor through which electricity from the energy harvester can enter or leave.

In further implementations, as described above, an implantable device may include a battery that is inductively chargeable by a power source external to the patient's body (e.g. via wireless power link 235). For example, in some implementations, a flexible, self-healing, rechargeable battery may include a reversible chemistry that will offer long lifespans as well as wireless inductive charging.

Accordingly, in some embodiments, a device implantable within a patient's body, comprises: a first member configured to be coupled to a first bone and a second member configured to be coupled to a second bone, the first and second members being operatively coupled to form a moveable joint; and a heating system operatively coupled to at least one of the first and second members and configured to controllably heat at least a portion of the at least one of the first and second members.

In some embodiments, the heating system includes a controller operatively coupled to a temperature sensor, the controller causing a heating element to apply heat when a lower temperature limit is sensed and to discontinue heating when an upper temperature limit is sensed. In further embodiments, the heating system includes a controller operable to receive one or more input signals indicative of one or more external conditions, the controller causing a heating element to apply heat based on the one or more external conditions.

And in some embodiments, the first and second members are operatively coupled to form at least one of a moveable hip joint, a moveable shoulder joint, or a moveable knee joint. In some embodiments, the heating system includes a power source that is wirelessly rechargeable.

And in some embodiments, the heating system includes a controller operatively coupled to a receiver configured to wirelessly receive an input signal, the controller being configured to causing a power driver to provide power to a heating element to apply heat based on the input signal. In further embodiments, the heating system includes a power source operatively coupled to the heating element and configured to provide power to a heating element to heat the at least a portion of the at least one of the first and second members.

And in still further embodiments, the heating system includes a receiver configured to wirelessly receive a heating power, and a receiver circuit operatively coupled the receiver and to the heating element, the receiver circuit being configured to provide the heating power to a heating element to heat the at least a portion of the at least one of the first and second members. In some embodiments, the heating system includes a receiver configured to wirelessly receive a heating power, and a receiver circuit operatively coupled the receiver and to a power supply, the receiver circuit being configured to provide the heating power to charge the power supply.

And in some embodiments, a system comprises: an implantable joint configured to be implanted within a patient's body, the implantable joint including a first member configured to be coupled to a first bone and a second member configured to be coupled to a second bone, the first and second members being operatively coupled to form a moveable joint that enables movement of the first bone relative to the second bone; and a heating system operatively coupled to at least one of the first and second members, the heating system including a main module that includes a power supply operatively coupled to a controller; and at least one heating element operatively coupled to the main module and to at least one of the first member and the second member, the at least one heating element being configured to receive power from the main module to heat at least a portion of the at least one of the first member and the second member.

In some embodiments, the main module further includes a temperature sensor operatively coupled to the controller and configured to sense a temperature proximate the at least one heating element, the controller being configured to cause the at least one heating element to apply heat when a lower temperature limit is sensed and to discontinue heating when an upper temperature limit is sensed. And in some embodiments, the controller is configured operable to receive one or more input signals indicative of one or more external conditions, the controller selectively causing power to be provided to the at least one heating element based on the one or more external conditions. For example, in some embodiments, the one or more external conditions include at least one of a temperature, a humidity, a barometric pressure, a time of day, or an activity level of a person.

In some embodiments, the main module includes a receiver configured to wirelessly receive an input signal, and a power driver operatively coupled to the at least one heating element, the controller being configured to cause the power driver to provide power to the at least one heating element based on the input signal. And in some embodiments, the main module includes a receiver configured to wirelessly receive a heating power, and a power driver operatively coupled to the at least one heating element, the controller being configured to cause the power driver to provide the heating power to the at least one heating element. In still further embodiments, the main module includes a receiver configured to wirelessly receive a heating power, and a receiver circuit operatively coupled the receiver and to the power supply, the receiver circuit being configured to provide the heating power to charge the power supply.

In some embodiments, the main module includes a resonant receiver configured to wirelessly receive a heating power, the system further comprising a power pack that includes a power pack battery operatively coupled to a resonant transmitter, the resonant transmitter being configured to wirelessly transmit the heating power to the resonant receiver to provide power to the heating system. And in some embodiments, the system further includes a power pack having a sensor configured to sense one or more external conditions and to transmit an input signal to the heating system indicative of the one or more external conditions, the controller being configured to at least one of apply or discontinue heating by the at least one heating element based on the input signal.

In still further embodiments, a system includes a monitoring module configured to wirelessly communicate with the implantable joint and to monitor one or more operating conditions and to transmit an input signal to the heating system, the controller being configured to at least one of apply or discontinue heating by the at least one heating element based on the input signal. And in some embodiments, the main module includes at least one fuse operatively coupled between the power supply and the at least one heating element, the at least one fuse being configured to discontinue heating by the at least one heating element based on or more operating conditions.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A device implantable within a patient's body, comprising:
   a first member configured to be coupled to a first bone and a second member configured to be coupled to a second bone, the first and second members being operatively coupled to form a moveable joint; and
   a heating system operatively coupled to at least one of the first and second members and configured to controllably heat at least a portion of the at least one of the first and second members, wherein the heating system includes a controller operable to receive one or more input signals indicative of one or more external conditions, the controller causing a heating element to apply heat based on the one or more external conditions.

2. The device of claim 1, wherein the heating system includes a controller operatively coupled to a temperature sensor, the controller causing a heating element to apply heat when a lower temperature limit is sensed and to discontinue heating when an upper temperature limit is sensed.

3. The device of claim 1, wherein the first and second members are operatively coupled to form at least one of a moveable hip joint, a moveable shoulder joint, or a moveable knee joint.

4. The device of claim 1, wherein the heating system includes a power source that is wirelessly rechargeable.

5. The device of claim 1, wherein the controller is operatively coupled to a receiver configured to wirelessly receive the one or more input signals, the controller being configured to cause a power driver to provide power to the heating element to apply heat based on the one or more input signals.

6. The device of claim 1, wherein the heating system includes a power source operatively coupled to the heating element and configured to provide power to the heating element to heat the at least a portion of the at least one of the first and second members.

7. The device of claim 1, wherein the heating system includes a receiver configured to wirelessly receive a heating power, and a receiver circuit operatively coupled to the receiver and to a heating element, the receiver circuit being configured to provide the heating power to the heating element to heat the at least a portion of the at least one of the first and second members.

8. The device of claim 1, wherein the heating system includes a receiver configured to wirelessly receive a heating power, and a receiver circuit operatively coupled to the receiver and to a power supply, the receiver circuit being configured to provide the heating power to charge the power supply.

9. A system, comprising:
   an implantable joint configured to be implanted within a patient's body, the implantable joint including:
      a first member configured to be coupled to a first bone and a second member configured to be coupled to a second bone, the first and second members being operatively coupled to form a moveable joint that enables movement of the first bone relative to the second bone; and a heating system operatively coupled to and disposed at least partially within at least one of the first and second members, the heating system including:
  a main module that includes a power supply operatively coupled to a controller; and
  at least one heating element operatively coupled to the main module and to at least one of the first member and the second members, the at least one heating element being configured to receive power from the power supply to heat at least a portion of the at least one of the first member and the second members,
  wherein the main module further includes a temperature sensor operatively coupled to the controller and configured to sense a temperature proximate the at least one heating element, the controller being configured to cause the at least one heating element to apply heat when a lower temperature limit is sensed and to discontinue heating when an upper temperature limit is sensed.

10. The system of claim 9, wherein the controller is operable to receive one or more input signals indicative of one or more external conditions, the controller selectively causing power to be provided to the at least one heating element based on the one or more external conditions.

11. The system of claim 10, wherein the one or more external conditions include at least one of a temperature, a humidity, a barometric pressure, a time of day, or an activity level of a person.

12. The system of claim 9, wherein the main module includes a receiver configured to wirelessly receive an input signal, and a power driver operatively coupled to the at least one heating element, the controller being configured to cause the power driver to provide power to the at least one heating element based on the input signal.

13. The system of claim 9, wherein the main module includes a receiver configured to wirelessly receive a heating power, and a power driver operatively coupled to the at least one heating element, the controller being configured to cause the power driver to provide the heating power to the at least one heating element.

14. The system of claim 9, wherein the main module includes a receiver configured to wirelessly receive a heating power, and a receiver circuit operatively coupled to the receiver and to the power supply, the receiver circuit being configured to provide the heating power to charge the power supply.

15. The system of claim 9, wherein the main module includes a resonant receiver configured to wirelessly receive a heating power, the system further comprising a power pack battery operatively coupled to a resonant transmitter, the resonant transmitter being configured to wirelessly transmit the heating power to the resonant receiver to provide power to the heating system.

16. The system of claim 9, further comprising a power pack having a sensor configured to sense one or more external conditions and to transmit an input signal to the heating system indicative of the one or more external conditions, the controller being configured to at least one of apply or discontinue heating by the at least one heating element based on the input signal.

17. The system of claim 9, further comprising a monitoring module configured to wirelessly communicate with the implantable joint and to monitor one or more operating conditions and to transmit an input signal to the heating system, the controller being configured to at least one of apply or discontinue heating by the at least one heating element based on the input signal.

18. The system of claim 9, wherein the main module includes at least one fuse operatively coupled between the power supply and the at least one heating element, the at least one fuse being configured to discontinue heating by the at least one heating element based on or more operating conditions.

19. A device implantable within a patient's body, comprising:
  a first member configured to be coupled to a first bone and a second member configured to be coupled to a second bone, the first and second members being operatively coupled to form a moveable joint; and
  a heating system heating system operatively coupled to at least one of the first and second members and configured to controllably heat at least a portion of the at least one of the first and second members, wherein the heating system includes a receiver configured to wirelessly receive a heating power, and a receiver circuit operatively coupled to the receiver and to a heating element, the receiver circuit being configured to provide the heating power to the heating element to heat the at least a portion of the at least one of the first and second members.

20. A method of heating a device disposed within a patient's body, comprising:
  implanting the device in vivo within the patient's body, the device including at least:
    a first member configured to be coupled to a first bone and a second member configured to be coupled to a second bone, the first and second members being operatively coupled to form a moveable joint; and
    a heating system that includes a power supply operatively coupled to and disposed at least partially within at least one of the first and second members and configured to controllably heat at least a portion of the at least one of the first and second members; and
  heating the at least a portion of the at least one of the first and second members of the device using power from the power supply;
  sensing one or more conditions; and
  controllably adjusting the heating applied by the heating system based on the sensed one or more conditions.

21. The method of claim 20, further comprising wirelessly recharging the power supply from a power source disposed external to the patient's body.

22. The method of claim 20, wherein the one or more conditions comprise at least one of an external condition or an operating condition.

* * * * *